(12) United States Patent
Weydt et al.

(10) Patent No.: US 12,354,745 B2
(45) Date of Patent: *Jul. 8, 2025

(54) PREDICTION BASED DELIVERING OR GUIDING OF THERAPY FOR DIABETES

(71) Applicant: Medtronic MiniMed, Inc., Northridge, CA (US)

(72) Inventors: Patrick E. Weydt, Moorpark, CA (US); Pratik J. Agrawal, Porter Ranch, CA (US); Louis J. Lintereur, Boise, ID (US); Lavie Golenberg, Bloomfield Hills, MI (US); David Dunleavy, West Hills, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 283 days.

This patent is subject to a terminal disclaimer.

(21) Appl. No.: 18/067,417

(22) Filed: Dec. 16, 2022

(65) Prior Publication Data
US 2023/0121873 A1    Apr. 20, 2023

Related U.S. Application Data

(63) Continuation of application No. 17/004,951, filed on Aug. 27, 2020, now Pat. No. 11,551,812.
(Continued)

(51) Int. Cl.
*G16H 40/67* (2018.01)
*A61B 5/00* (2006.01)
(Continued)

(52) U.S. Cl.
CPC ......... *G16H 40/67* (2018.01); *A61B 5/14532* (2013.01); *A61B 5/7405* (2013.01);
(Continued)

(58) Field of Classification Search
None
See application file for complete search history.

(56) References Cited

U.S. PATENT DOCUMENTS

| 7,935,076 B2 | 5/2011 | Estes et al. |
| 9,008,803 B2 | 4/2015 | Blomquist |

(Continued)

FOREIGN PATENT DOCUMENTS

| CN | 109789264 A | 5/2019 |
| EP | 3417773 A1 | 12/2018 |

(Continued)

OTHER PUBLICATIONS

Castle et al., "Future of Automated Insulin Delivery Systems," Diabetes Technology & Therapeutics, vol. 19, Supplement 3, Jun. 1, 2017, 6 pp.
(Continued)

*Primary Examiner* — Manuel A Mendez
(74) *Attorney, Agent, or Firm* — Weaver Austin Villeneuve & Sampson LLP

(57) ABSTRACT

An example system for therapy delivery includes one or more processors configured to in response to a prediction indicating that the meal event is to occur, output instructions to an insulin delivery device to deliver a partial therapy dosage, to a device to notify the patient to use the insulin delivery device to take the partial therapy dosage, or to the insulin delivery device to prepare the partial therapy dosage prior to the meal event occurring, and in response to a determination indicating that the meal event is occurring (e.g., based on movement characteristics of a patient arm), output instructions to the insulin delivery device to deliver a remaining therapy dosage, to the device to notify the patient to use the insulin delivery device to take the remain-
(Continued)

ing therapy dosage, or to the insulin delivery device to prepare the remaining therapy dosage.

20 Claims, 8 Drawing Sheets

Related U.S. Application Data

(60) Provisional application No. 62/893,717, filed on Aug. 29, 2019, provisional application No. 62/893,722, filed on Aug. 29, 2019.

(51) Int. Cl.
| | |
|---|---|
| *A61B 5/145* | (2006.01) |
| *A61K 38/28* | (2006.01) |
| *A61M 5/142* | (2006.01) |
| *A61M 5/172* | (2006.01) |
| *G06F 3/01* | (2006.01) |
| *G06N 3/08* | (2023.01) |
| *G16H 20/17* | (2018.01) |
| *G16H 20/60* | (2018.01) |
| *G16H 40/20* | (2018.01) |
| *G16H 70/40* | (2018.01) |
| *H04W 4/02* | (2018.01) |
| *H04M 1/72454* | (2021.01) |
| *H04M 1/72463* | (2021.01) |

(52) U.S. Cl.
CPC .............. *A61B 5/746* (2013.01); *A61K 38/28* (2013.01); *A61M 5/14244* (2013.01); *A61M 5/14248* (2013.01); *A61M 5/1723* (2013.01); *G06F 3/017* (2013.01); *G06N 3/08* (2013.01); *G16H 20/17* (2018.01); *G16H 20/60* (2018.01); *G16H 40/20* (2018.01); *G16H 70/40* (2018.01); *H04W 4/027* (2013.01); A61M 2205/3584 (2013.01); A61M 2205/502 (2013.01); A61M 2205/505 (2013.01); A61M 2205/52 (2013.01); A61M 2205/581 (2013.01); A61M 2205/582 (2013.01); A61M 2205/583 (2013.01); A61M 2205/8206 (2013.01); A61M 2230/201 (2013.01); A61M 2230/63 (2013.01); *H04M 1/72454* (2021.01); *H04M 1/72463* (2021.01)

(56) References Cited

U.S. PATENT DOCUMENTS

| | | | |
|---|---|---|---|
| 9,037,125 B1 | 5/2015 | Kadous | |
| 10,080,840 B2 | 9/2018 | Gescheit et al. | |
| 10,258,745 B2 | 4/2019 | Despa et al. | |
| 10,307,538 B2 | 6/2019 | Desborough et al. | |
| 11,551,812 B2 * | 1/2023 | Weydt ................. | A61M 5/1723 |
| 11,710,562 B2 | 7/2023 | Weydt et al. | |
| 11,990,236 B2 | 5/2024 | Weydt et al. | |
| 2013/0217990 A1 | 8/2013 | Saettel et al. | |
| 2014/0012510 A1 | 1/2014 | Mensinger et al. | |
| 2014/0184772 A1 | 7/2014 | Hanina et al. | |
| 2014/0315162 A1 | 10/2014 | Ehrenkranz | |
| 2015/0246179 A1 | 9/2015 | Zur et al. | |
| 2016/0306932 A1 | 10/2016 | Fateh et al. | |
| 2017/0053552 A1 | 2/2017 | Zhong et al. | |
| 2017/0150360 A1 | 5/2017 | Caldwell et al. | |
| 2017/0189625 A1 | 7/2017 | Cirillo et al. | |
| 2017/0203030 A1 | 7/2017 | Brewer et al. | |
| 2017/0203039 A1 | 7/2017 | Desborough et al. | |
| 2017/0228518 A1 | 8/2017 | Booth et al. | |
| 2017/0249445 A1 | 8/2017 | Devries et al. | |
| 2017/0257844 A1 | 9/2017 | Miller et al. | |
| 2017/0311903 A1 | 11/2017 | Davis et al. | |
| 2017/0332347 A1 | 11/2017 | Boss et al. | |
| 2018/0109412 A1 | 4/2018 | Xuan et al. | |
| 2018/0147362 A1 | 5/2018 | Arenas Latorre et al. | |
| 2018/0214077 A1 | 8/2018 | Dunki-Jacobs et al. | |
| 2018/0271418 A1 | 9/2018 | Hayter et al. | |
| 2019/0052748 A1 | 2/2019 | Stewart | |
| 2019/0158447 A1 | 5/2019 | Aggarwal et al. | |
| 2019/0182749 A1 | 6/2019 | Breaux et al. | |
| 2019/0236465 A1 | 8/2019 | Vleugels | |
| 2019/0246914 A1 | 8/2019 | Canstantin et al. | |
| 2019/0252079 A1 | 8/2019 | Constantin et al. | |
| 2019/0274624 A1 | 9/2019 | Mazlish et al. | |
| 2019/0382025 A1 | 12/2019 | Mena Benito et al. | |
| 2020/0129099 A1 | 4/2020 | Mi et al. | |
| 2020/0135320 A1 | 4/2020 | Vleugels | |
| 2020/0152312 A1 | 5/2020 | Connor | |
| 2021/0060247 A1 | 3/2021 | Weydt et al. | |
| 2021/0065894 A1 | 3/2021 | Weydt et al. | |
| 2023/0317277 A1 | 10/2023 | Weydt et al. | |
| 2024/0257965 A1 | 8/2024 | Weydt et al. | |

FOREIGN PATENT DOCUMENTS

| | | |
|---|---|---|
| KR | 20180028823 A | 3/2018 |
| WO | 2014115025 A1 | 7/2014 |
| WO | 2017027258 A1 | 2/2017 |

OTHER PUBLICATIONS

Gomez-Peralta et al., "A Novel Insulin Delivery Optimization and Tracking System," Diabetes Technology & Therapeutics, vol. 21, No. 4, Apr. 4, 2019, 6 pp.
International Preliminary Report on Patentability from International Application No. PCT/US2020/048446, dated Mar. 10, 2022, 9 pp.
International Search Report and Written Opinion of International Application No. PCT/US2020/048446, mailed Nov. 20, 2020, 15 pp.
Notice of Allowance from U.S. Appl. No. 17/004,951 dated Sep. 15, 2022, 8 pp.
Communication pursuant to Rules 161(1) and 162 EPC from counterpart European Application No. 20771398.3 dated Apr. 5, 2022, 3 pp.
Response to Communication pursuant to Rules 161(1) and 162 EPC dated Apr. 5, 2022, from counterpart European Application No. 20771398.3, filed Aug. 10, 2022, 15 pp.
CN Office Action dated Nov. 29, 2024 in CN Application No. 202080059875.2, with English translation [MEDTP121].
EP Office Action dated Aug. 9, 2024, in EP Application No. 20771398.3 [MEDTP109].
International Preliminary Report on Patentability dated Mar. 10, 2022 in PCT Application No. PCT/US2020/048461.
International Search Report and Written Opinion dated Nov. 6, 2020 in PCT Application No. PCT/US2020/048461.
Shivers J., et al., "Turn It Off: Diabetes Device Alarm Fatigue Considerations for the Present and the Future," Journal of Diabetes Science and Technology, May 2013, vol. 7 (3), pp. 789-794.
U.S. Advisory Action dated Dec. 13, 2023 in U.S. Appl. No. 17/004,981 [MEDTP120US].
U.S. Final Office Action dated Oct. 27, 2023 in U.S. Appl. No. 17/004,981 [MEDTP120US].
U.S. Non-Final Office Action dated Jul. 6, 2023, in U.S. Appl. No. 17/004,981 [MEDTP120US].
U.S. Notice of Allowance dated Jan. 23, 2024 in U.S. Appl. No. 17/004,981 [MEDTP120US].
U.S. Office Action dated Sep. 15, 2022, in U.S. Appl. No. 17/004,951 [A0002725US03].

* cited by examiner

PREDICTION BASED DELIVERING OR GUIDING OF THERAPY FOR DIABETES

This application is a continuation of U.S. application Ser. No. 17/004,951, filed Aug. 27, 2020, which claims the benefit of U.S. Provisional Application No. 62/893,717, filed Aug. 29, 2019, and U.S. Provisional Application No. 62/893,722, filed Aug. 29, 2019, the entire content of each of which is hereby incorporated by reference.

TECHNICAL FIELD

The disclosure relates to medical systems and, more particularly, to medical systems for therapy for diabetes.

BACKGROUND

A patient with diabetes receives insulin from a pump or injection device to control the glucose level in his or her bloodstream. Naturally produced insulin may not control the glucose level in the bloodstream of a diabetes patient due to insufficient production of insulin and/or due to insulin resistance. To control the glucose level, a patient's therapy routine may include dosages of basal insulin and bolus insulin. Basal insulin, also called background insulin, tends to keep blood glucose levels at consistent levels during periods of fasting and is a long acting or intermediate acting insulin. Bolus insulin may be taken specifically at or near meal times or other times where there may be a relatively fast change in glucose level, and may therefore serve as a short acting or rapid acting form of insulin dosage.

SUMMARY

Devices, systems, and techniques for managing glucose level in a patient are described. For example, one or more processors (e.g., in one or more servers in a network cloud, in a patient device, and/or on a pump for insulin delivery) may determine that a meal event is to occur or is occurring. In response to the determination that a meal event is to occur, the patient may take a portion of the insulin that is to be delivered to the patient prior to the meal occurring. For example, the one or more processors may output instructions to a pump, instructing the pump to deliver a partial therapy dosage (e.g., portion of the insulin) or output instructions to the patient device, instructing the patient device to output a notification to the patient to inject a partial therapy dosage. The one or more processors may be configured to determine the amount and timing of delivery of the partial therapy dosage, such as based on past patient behavior. The patient may then take a remaining therapy dosage (e.g., remaining portion of the insulin for the meal) after the meal. By onboarding at least a portion of the insulin (e.g., pre-dosing before a meal), the chances of there being an undesirable high glucose level immediately after the meal are reduced. Also, because the patient took a portion of the therapy dosage of insulin, instead of the entire dosage of insulin, the changes of there being an undesirable low glucose level is also reduced (e.g., in the event the patient does not eat).

In one example, the disclosure describes a system for therapy delivery, the system comprising one or more processors configured to predict that a meal event is to occur, in response to the prediction indicating that the meal event is to occur, output instructions to at least one of: (1) an insulin delivery device to cause the insulin delivery device to deliver a partial therapy dosage prior to the meal event occurring, (2) to a device to notify the patient to use the insulin delivery device to take the partial therapy dosage prior to the meal event occurring, or (3) to the insulin delivery device to cause the insulin delivery device to prepare the partial therapy dosage prior to the meal event occurring, determine that the meal event is occurring based on one or more movement characteristics of movement of an arm of the patient, and in response to the determination indicating that the meal event is occurring, output instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

In one example, the disclosure describes predicting, with one or more processors, that a meal event is to occur, in response to the prediction indicating that the meal event is to occur, outputting, with the one or more processors, instructions to at least one of: (1) an insulin delivery device to cause the insulin delivery device to deliver a partial therapy dosage prior to the meal event occurring, (2) to a device to notify the patient to use the insulin delivery device to take the partial therapy dosage prior to the meal event occurring, or (3) to the insulin delivery device to cause the insulin delivery device to prepare the partial therapy dosage prior to the meal event occurring, determining, with the one or more processors, that the meal event is occurring based on one or more movement characteristics of movement of an arm of the patient, and in response to the determination indicating that the meal event is occurring, outputting, with the one or more processors, instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

In one example, the disclosure describes a computer-readable storage medium storing instructions thereon that when executed cause one or more processors to predict that a meal event is to occur, in response to the prediction indicating that the meal event is to occur, output instructions to at least one of: (1) the insulin delivery device to deliver a partial therapy dosage prior to the meal event occurring, (2) to the device to notify the patient to use the insulin delivery device to take the partial therapy dosage prior to the meal event occurring, or (3) to the insulin delivery device to cause the insulin delivery device to prepare the partial therapy dosage prior to the meal event occurring, determine that the meal event is occurring based on one or more movement characteristics of movement of an arm of the patient, and in response to the determination indicating that the meal event is occurring, output instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

The details of one or more aspects of the disclosure are set forth in the accompanying drawings and the description below. Other features, objects, and advantages of this disclosure will be apparent from the description and drawings, and from the claims.

DETAILED DESCRIPTION

Figure 1:
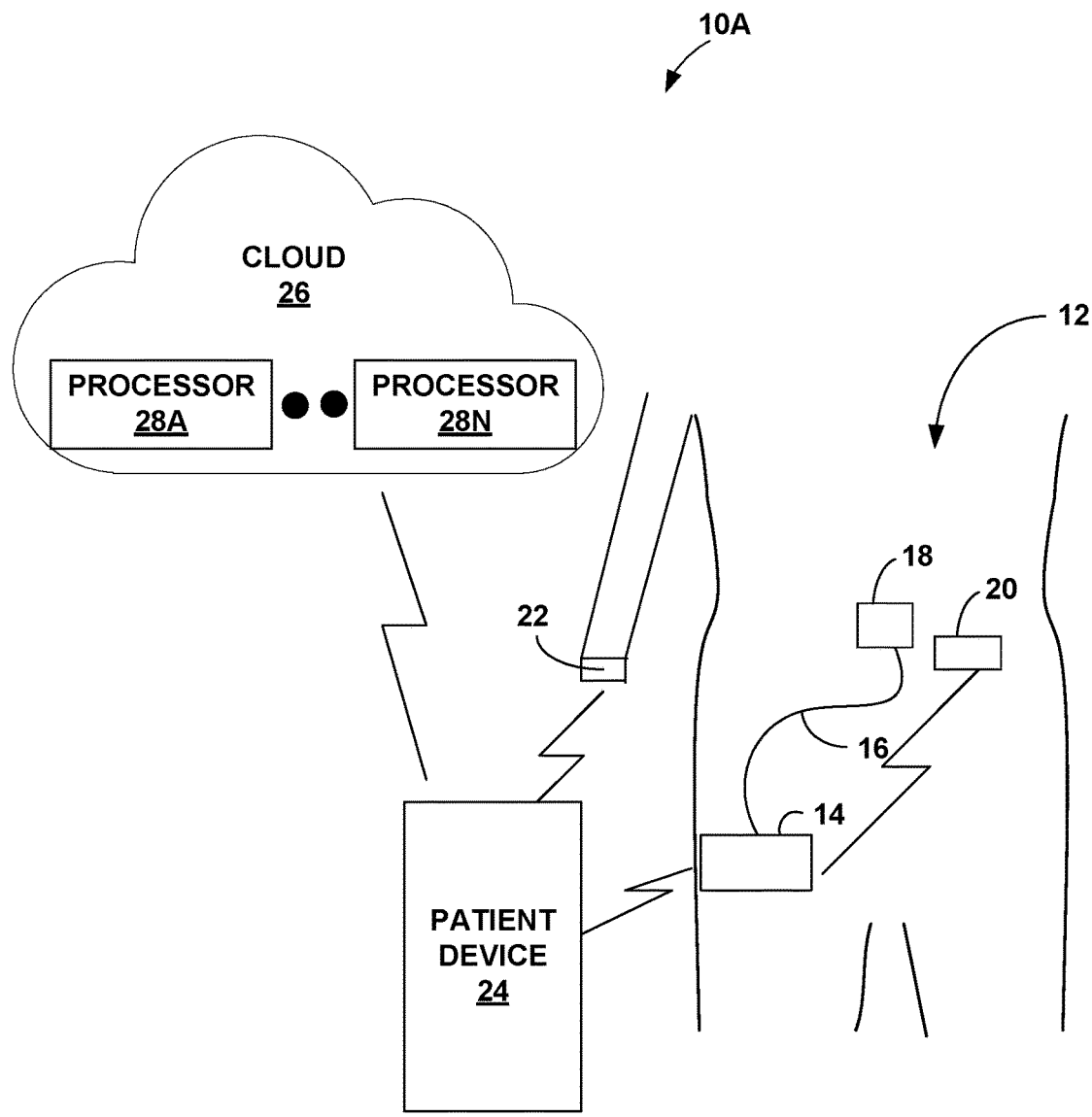
FIG. 1 is a block diagram illustrating an example system for delivering or guiding therapy dosage, in accordance with one or more examples described in this disclosure.

Devices, systems, and techniques for managing glucose level in a patient are described in this disclosure. A patient with diabetes may take basal insulin (e.g., slow or intermediate acting insulin) and supplement the basal insulin with bolus insulin (e.g., rapid or short acting insulin). For example, the patient may take a therapy dosage of bolus insulin after, before, or during a meal or some other activity, where there is a chance that the glucose level in the patient will increase relatively quickly toward an undesirably high glucose level, causing hyperglycemia. However, taking too large a therapy dosage of bolus insulin may result in an undesirably low glucose level, causing hypoglycemia.

In some cases, patients may forget to take a bolus insulin dosage prior to, during, or subsequent to meals, or may take the bolus insulin dosage, forget they took the bolus insulin dosage, and then inadvertently take another bolus insulin dosage. This disclosure describes example techniques that may preemptively determine whether a patient is to receive insulin therapy and an amount of therapy that is to be received prior to a meal event or other activity based on patient patterns. As one example, one or more processors (e.g., in one or more servers in a network cloud, in a patient device, and/or on a pump for insulin delivery) may utilize artificial intelligence, such as machine-learning models, to predict that a patient is about to eat. For instance, if the patient tends to eat at a regular time, the one or more processors may determine the patient is about to eat based at least in part on time of day. If the location, e.g., global positioning system (GPS) location, of the patient (e.g., based on output from the patient device) indicates that the patient is near a restaurant, cafeteria, or other eating location, the one or more processors may determine that the patient is about to eat based on location.

The one or more processors, based on a determination that a meal event is to occur, may output instructions to an insulin delivery device (e.g., pump or injection device) to cause the insulin delivery device to automatically deliver a partial therapy dosage prior to the meal event or output an alert (e.g., instructions) to a device to notify the patient to use the insulin delivery device (e.g., pump or injection device) to take the partial therapy dosage prior to the meal even occurring. As described below, the device may the device that includes the one or more processors. If a patient is to take X amount of bolus insulin in association with a meal event, the partial therapy dosage may be Y amount of bolus insulin, where Y is less than X.

By pre-delivering or pre-dosing insulin prior to the meal, the chances of a postprandial high glucose level (i.e., high glucose level following a meal) may be reduced. Example ranges of time period prior to the meal include 5 minutes, 10 minutes, 15 minutes, 20 minutes, 25 minutes, or 30 minutes. However, other ranges are possible as well. In some examples, the amount of time prior to the meal may be based on the type of meal the patient is predicted to eat. For instance, if the patient is predicted to eat a meal with a relatively high amount of carbohydrates, the amount of time prior to the meal that the patient receives the partial therapy dosage of insulin may be different than if the patient is predicted to eat a meal with a relatively low amount of carbohydrates.

Also, by delivering a partial therapy dosage, rather than an entire therapy dosage, the chances of an adverse effect, such as hypoglycemia, in the event the patient does not eat is reduced. In some examples, the one or more processors may confirm that the patient consumed the meal, and in response deliver the remaining therapy dosage.

There may be various ways in which to cause the insulin delivery device to deliver the partial therapy dosage prior to the meal event. As one example, the one or more processors may specify to the insulin delivery device an amount of bolus insulin to deliver, and in response, the insulin delivery device may deliver the specified amount of insulin. In some cases, the specified amount of insulin may be a particular fixed unit of bolus, and the one or more processors may specify that a unit of bolus insulin is to be delivered. As another example, the one or more processors may specify a glucose level to the insulin delivery device, and in response, the insulin delivery device may deliver insulin determined to be sufficient to cause the patient to reach the specified glucose level.

In one or more examples, one or more processors may determine that the meal event is occurring. For example, one or more processors of a wearable device (e.g., smartwatch) may detect one or more movement characteristics associated with movement of the patient's hand, such as values relating to frequency, amplitude, trajectory, position, velocity, acceleration and/or pattern of movement instantaneously or over time. The frequency of movement of the patient's arm may refer to how many times the patient repeated a movement within a certain time (e.g., such as frequency of movement back and forth between two positions). The one or more processors may receive the information of the one or more movement characteristics of the patient's hand and determine that the patient is eating based on the received information (e.g., the frequency and manner of movement of the patient's hand aligns with frequency and manner of movement of someone that is eating). In response to the determination indicating that the meal event is occurring, the one or more processors may output instructions to at least one of the insulin delivery device to deliver a remaining therapy dosage, the device to deliver a recommended therapy dosage to at least one of the insulin deliver device, or to the device to notify the patient to use the insulin delivery device to take the remaining therapy dosage. For instance, if a patient is to take X amount of bolus insulin, and the partial therapy dosage is Y amount of bolus insulin, then the remaining therapy dosage (Z) is the difference between X and Y (i.e., Z=X−Y). In some examples, Z is bigger than Y.

FIG. 1 is a block diagram illustrating an example system for delivering or guiding therapy dosage, in accordance with one or more examples described in this disclosure. FIG. 1 illustrates system 10A that includes patient 12, insulin pump 14, tubing 16, infusion set 18, sensor 20 (e.g., glucose sensor), wearable device 22, patient device 24, and cloud 26. Cloud 26 represents a local, wide area or global computing network including one or more processors 28A-28N ("one or more processors 28"). In some examples, the various components may determine changes to therapy based on determination of glucose level for sensor 20, and therefore system 10A may be referred to as a continuous glucose monitoring (CGM) system 10A.

Patient 12 may be diabetic (e.g., Type 1 diabetic or Type 2 diabetic), and therefore, the glucose level in patient 12 may be uncontrolled without delivery of supplemental insulin. For example, patient 12 may not produce sufficient insulin to control the glucose level or the amount of insulin that patient 12 produces may not be sufficient due to insulin resistance that patient 12 may have developed.

To receive the supplemental insulin, patient 12 may carry insulin pump 14 that couples to tubing 16 for delivery of insulin into patient 12. Infusion set 18 may connect to the skin of patient 12 and include a cannula to deliver insulin into patient 12. Sensor 20 may also be coupled to patient 12 to measure glucose level in patient 12. Insulin pump 14, tubing 16, infusion set 18, and sensor 20 may together form an insulin pump system. One example of the insulin pump system is the MINIMED™ 670G INSULIN PUMP SYSTEM by Medtronic, Inc. However, other examples of insulin pump systems may be used and the example techniques should not be considered limited to the MINIMED™ 670G INSULIN PUMP SYSTEM. For example, the techniques described in this disclosure may be utilized in insulin pump systems that include wireless communication capabilities. However, the example techniques should not be considered limited to insulin pump systems with wireless communication capabilities, and other types of communication, such as wired communication, may be possible. In another example, insulin pump 14, tubing 16, infusion set 18, and/or sensor 20 may be contained in the same housing.

Insulin pump 14 may be a relatively small device that patient 12 can place in different locations. For instance, patient 12 may clip insulin pump 14 to the waistband of pants worn by patient 12. In some examples, to be discreet, patient 12 may place insulin pump 14 in a pocket. In general, insulin pump 14 can be worn in various places and patient 12 may place insulin pump 14 in a location based on the particular clothes patient 12 is wearing.

To deliver insulin, insulin pump 14 includes one or more reservoirs (e.g., two reservoirs). A reservoir may be a plastic cartridge that holds up to N units of insulin (e.g., up to 300 units of insulin) and is locked into insulin pump 14. Insulin pump 14 may be a battery powered device that is powered by replaceable and/or rechargeable batteries.

Tubing 16, sometimes called a catheter, connects on a first end to a reservoir in insulin pump 14 and connects on a second end to infusion set 18. Tubing 16 may carry the insulin from the reservoir of insulin pump 14 to patient 12. Tubing 16 may be flexible, allowing for looping or bends to minimize concern of tubing 16 becoming detached from insulin pump 14 or infusion set 18 or concern from tubing 16 breaking.

Infusion set 18 may include a thin cannula that patient 12 inserts into a layer of fat under the skin (e.g., subcutaneous connection). Infusion set 18 may rest near the stomach of patient 12. The insulin travels from the reservoir of insulin pump 14, through tubing 16, and through the cannula in infusion set 18, and into patient 12. In some examples, patient 12 may utilize an infusion set insertion device.

Patient 12 may place infusion set 18 into the infusion set insertion device, and with a push of a button on the infusion set insertion device, the infusion set insertion device may insert the cannula of infusion set 18 into the layer of fat of patient 12, and infusion set 18 may rest on top of the skin of the patient with the cannula inserted into the layer of fat of patient 12.

Sensor 20 may include a sensor that is inserted under the skin of patient 12, such as near the stomach of patient 12 or in the arm of patient 12 (e.g., subcutaneous connection). The sensor of sensor 20 may be configured to measure the interstitial glucose level, which is the glucose found in the fluid between the cells of patient 12. Sensor 20 may be configured to continuously or periodically sample the glucose level and rate of change of the glucose level over time.

In one or more examples, insulin pump 14, sensor 20, and the various components illustrated in FIG. 1, may together form a closed-loop therapy delivery system. For example, patient 12 may set a target glucose level, usually measured in units of milligrams per deciliter, on insulin pump 14. Insulin pump 14 may receive the current glucose level from sensor 20, and in response may increase or decrease the amount of insulin delivered to patient 12. For example, if the current glucose level is higher than the target glucose level, insulin pump 14 may increase the insulin. If the current glucose level is lower than the target glucose level, insulin pump 14 may temporarily cease delivery of the insulin. Insulin pump 14 may be considered as an example of an automated insulin delivery (AID) device. Other examples of AID devices may be possible, and the techniques described in this disclosure may be applicable to other AID devices.

For example, insulin pump 14 and sensor 20 may be configured to operate together to mimic some of the ways in which a healthy pancreas works. Insulin pump 14 may be configured to deliver basal insulin, which is a small amount of insulin released continuously throughout the day. There may be times when glucose levels increase, such as due to eating or some other activity that patient 12 undertakes. Insulin pump 14 may be configured to deliver bolus insulin on demand in association with food intake or to correct an undesirably high glucose level in the bloodstream. In one or more examples, if the glucose level rises above a target level, then insulin pump 14 may increase the bolus insulin to address the increase in glucose level. Insulin pump 14 may be configured to compute basal and bolus insulin delivery, and deliver the basal and bolus insulin accordingly. For instance, insulin pump 14 may determine the amount of basal insulin to deliver continuously, and then determine the amount of bolus insulin to deliver to reduce glucose level in response to an increase in glucose level due to eating or some other event.

Accordingly, in some examples, sensor 20 may sample glucose level and rate of change in glucose level over time. Sensor 20 may output the glucose level to insulin pump 14 (e.g., through a wireless link connection like Bluetooth or BLE). Insulin pump 14 may compare the glucose level to a target glucose level (e.g., as set by patient 12 or clinician), and adjust the insulin dosage based on the comparison. In some examples, sensor 20 may also output a predicted glucose level (e.g., where glucose level is expected to be in the next 30 minutes), and insulin pump 14 may adjust insulin delivery based on the predicted glucose level.

As described above, patient 12 or a clinician may set the target glucose level on insulin pump 14. There may be various ways in which patient 12 or the clinician may set the target glucose level on insulin pump 14. As one example, patient 12 or the clinician may utilize patient device 24 to communicate with insulin pump 14. Examples of patient device 24 include mobile devices, such as smartphones or tablet computers, laptop computers, and the like. In some examples, patient device 24 may be a special programmer or controller for insulin pump 14. Although FIG. 1 illustrates one patient device 24, in some examples, there may be a plurality of patient devices. For instance, system 10A may include a mobile device and a controller, each of which are examples of patient device 24. For ease of description only, the example techniques are described with respect to patient device 24, with the understanding that patient device 24 may be one or more patient devices.

Patient device 24 may also be configured to interface with sensor 20. As one example, patient device 24 may receive information from sensor 20 through insulin pump 14, where insulin pump 14 relays the information between patient device 24 and sensor 20. As another example, patient device 24 may receive information (e.g., glucose level or rate of change of glucose level) directly from sensor 20 (e.g., through a wireless link).

In one or more examples, patient device 24 may display a user interface with which patient 12 or the clinician may control insulin pump 14. For example, patient device 24 may display a screen that allows patient 12 or the clinician to enter the target glucose level. As another example, patient device 24 may display a screen that outputs the current and/or past glucose level. In some examples, patient device 24 may output notifications to patient 12, such as notifications if the glucose level is too high or too low, as well as notifications regarding any action that patient 12 needs to take. For example, if the batteries of insulin pump 14 are low on charge, then insulin pump 14 may output a low battery indication to patient device 24, and patient device 24 may in turn output a notification to patient 12 to replace or recharge the batteries.

Controlling insulin pump 14 through patient device 24 is one example, and should not be considered limiting. For example, insulin pump 14 may include a user interface (e.g., pushbuttons) that allow patient 12 or the clinician to set the various glucose levels of insulin pump 14. Also, in some examples, insulin pump 14 itself, or in addition to patient device 24, may be configured to output notifications to patient 12. For instance, if the glucose level is too high or too low, insulin pump 14 may output an audible or haptic output. As another example, if the battery is low, then insulin pump 14 may output a low battery indication on a display of insulin pump 14.

The above describes examples ways in which insulin pump 14 may deliver insulin to patient 12 based on the current glucose levels (e.g., as measured by sensor 20). In some cases, there may be therapeutic gains by proactively delivering insulin to patient 12, rather than reacting to when glucose levels become too high or too low.

The glucose level in patient 12 may increase due to particular user actions. As one example, the glucose level in patient 12 may increase due to patient 12 eating. In some examples, there may be therapeutic gains if it is possible to determine that patient 12 is eating, and delivering insulin based on the determination that patient 12 is eating.

For example, patient 12 may forget to cause insulin pump 14 to deliver insulin after eating, resulting an insulin shortfall. Alternatively, patient 12 may cause insulin pump 14 to deliver insulin after eating but may have forgotten that patient 12 previously caused insulin pump 14 to deliver insulin for the same meal event, resulting in an excessive insulin dosage. Also, in examples where sensor 20 is utilized, insulin pump 14 may not take any action until after the glucose level is greater than a target level. By proactively determining that patient 12 is eating, insulin pump 14 may be able to deliver insulin in such a manner that the glucose level does not rise above the target level or rises only slightly above the target level (i.e., rises by less than what the glucose level would have risen if insulin were not delivered proactively). In some cases, by proactively determining that patient 12 is eating and delivering insulin accordingly, the glucose level of patient 12 may increase more slowly.

Although the above describes proactive determination of patient 12 eating and delivering insulin accordingly, the example techniques are not so limited. The example techniques may be utilized for proactively determining an activity that patient 12 is undertaking (e.g., eating, exercising, sleeping, driving, etc.). Insulin pump 14 may then deliver insulin based on the determination of the type of activity patient 12 is undertaking.

As illustrated in FIG. 1, patient 12 may wear wearable device 22. Examples of wearable device 22 include a smartwatch or a fitness tracker, either of which may, in some examples, be configured to be worn on a patient's wrist or arm. In one or more examples, wearable device 22 includes inertial measurement unit, such as a six-axis inertial measurement unit. The six-axis inertial measurement unit may couple a 3-axis accelerometer with a 3-axis gyroscope. Accelerometers measure linear acceleration, while gyroscopes measure rotational motion. Wearable device 22 may be configured to determine one or more movement characteristics of patient 12. Examples of the one or more movement characteristics include values relating to frequency, amplitude, trajectory, position, velocity, acceleration and/or pattern of movement instantaneously or over time. The frequency of movement of the patient's arm may refer to how many times patient 12 repeated a movement within a certain time (e.g., such as frequency of movement back and forth between two positions).

Patient 12 may wear wearable device 22 on his or her wrist. However, the example techniques are not so limited. Patient 12 may wear wearable device 22 on a finger, forearm, or bicep. In general, patient 12 may wear wearable device 22 anywhere that can be used to determine gestures indicative of eating, such as movement characteristics of the arm.

The manner in which patient 12 is moving his or her arm (i.e., the movement characteristics) may refer to the direction, angle, and orientation of the movement of the arm of patient 12, including values relating to frequency, amplitude, trajectory, position, velocity, acceleration and/or pattern of movement instantaneously or over time. As an example, if patient 12 is eating, then the arm of patient 12 will be oriented in a particular way (e.g., thumb is facing towards the body of patient 12), the angle of movement of the arm will be approximately a 90-degree movement (e.g., starting from plate to mouth), and the direction of movement of the arm will be a path that follows from plate to mouth. The forward/backward, up/down, pitch, roll, yaw measurements from wearable device 22 may be indicative of the manner in which patient 12 is moving his or her arm. Also, patient 12 may have a certain frequency at which patient 12 moves his or her arm or a pattern at which patient 12 moves his or her arm that is more indicative of eating, as compared to other activities, like smoking or vaping, where patient 12 may raise his or her arm to his or her mouth.

Although the above description describes wearable device 22 as being utilized to determine whether patient 12 is eating, wearable device 22 may be configured to detect movements of the arm of patient 12 (e.g., one or more movement characteristics), and the movement characteristics may be utilized to determine an activity undertaken by patient 12. For instance, the movement characteristics detected by wearable device 22 may indicate whether patient 12 is exercising, driving, sleeping, etc. As another example, wearable device 22 may indicate posture of patient 12, which may align with a posture for exercising, driving, sleeping, eating, etc. Another term for movement characteristics may be gesture movements. Accordingly, wearable device 22 may be configured to detect gesture movements (i.e., movement characteristics of the arm of patient 12) and/or posture, where the gesture and/or posture may be part of various activities (e.g., eating, exercising, driving, sleeping, etc.).

In some examples, wearable device 22 may be configured to determine, based on the detected gestures (e.g., movement characteristics of the arm of patient 12) and/or posture, the particular activity patient 12 is undertaking. For example, wearable device 22 may be configured to determine whether patient 12 is eating, exercising, driving, sleeping, etc. In some examples, wearable device 22 may output information indicative of the movement characteristics of the arm of patient 12 and/or posture of patient 12 to patient device 24, and patient device 24 may be configured to determine the activity patient 12 is undertaking.

Wearable device 22 and/or patient device 24 may be programmed with information that wearable device 22 and/or patient device 24 utilize to determine the particular activity patient 12 is undertaking. For example, patient 12 may undertake various activities throughout the day where the movement characteristics of the arm of patient 12 may be similar to the movement characteristics of the arm of patient 12 for a particular activity, but patient 12 is not undertaking that activity. As one example, patient 12 yawning and cupping his or her mouth may have a similar movement as patient 12 eating. Patient 12 picking up groceries may have similar movement as patient 12 exercising. Also, in some examples, patient 12 may be undertaking a particular activity, but wearable device 22 and/or patient device 24 may fail to determine that patient 12 is undertaking the particular activity.

Accordingly, in one or more examples, wearable device 22 and/or patient device 24 may "learn" to determine whether patient 12 is undertaking a particular activity. However, the computing resources of wearable device 22 and patient device 24 may be insufficient to performing the learning needed to determine whether patient 12 is undertaking a particular activity. It may be possible for the computing resources of wearable device 26 and patient device 24 to be sufficient to perform the learning, but for ease of description only, the following is described with respect to one or more processors 28 in cloud 26.

As illustrated in FIG. 1, system 10A includes cloud 26 that includes one or more processors 28. For example, cloud 26 includes a plurality of network devices (e.g., servers), and the plurality of devices each include one or more processors. One or more processors 28 may be processors of the plurality of network devices, and may be located within a single one of the network devices, or may be distributed across two or more of the network devices. Cloud 26 represents a cloud infrastructure that supports one or more processors 28 on which applications or operations requested by one or more users run. For example, cloud 26 provides cloud computing for using one or more processors 28, to store, manage, and process data on the network devices, rather than by personal device 24 or wearable device 22. One or more processors 28 may share data or resources for performing computations, and may be part of computing servers, web servers, database servers, and the like. One or more processors 28 may be in network devices (e.g., servers) within a datacenter or may be distributed across multiple datacenters. In some cases, the datacenters may be in different geographical locations.

One or more processors 28, as well as other processing circuitry described herein, can include any one or more microprocessors, digital signal processors (DSPs), application specific integrated circuits (ASICs), field programmable gate arrays (FPGAs), or any other equivalent integrated or discrete logic circuitry, as well as any combinations of such components. The functions attributed one or more processors 28, as well as other processing circuitry described herein, herein may be embodied as hardware, firmware, software or any combination thereof.

One or more processors 28 may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. One or more processors 28 may include arithmetic logic units (ALUs), elementary function units (EFUs), digital circuits, analog circuits, and/or programmable cores, formed from programmable circuits. In examples where the operations of one or more processors 28 are performed using software executed by the programmable circuits, memory (e.g., on the servers) accessible by one or more processors 28 may store the object code of the software that one or more processors 28 receive and execute.

In some examples, one or more processors 28 may be configured to determine patterns from gesture movements (e.g., as one or more movement characteristics determined by wearable device 22), and configured to determine a particular activity patient 12 is undertaking. One or more processors 28 may provide responsive real-time cloud services that can, on a responsive real-time basis, determine the activity patient 12 is undertaking, and in some examples, provide recommended therapy (e.g., insulin dosage amount). Cloud 26 and patient device 24 may communicate via Wi-Fi or through a carrier network.

For example, as described above, in some examples, wearable device 22 and/or patient device 24 may be configured to determine that patient 12 is undertaking an activity. However, in some examples, patient device 24 may output information indicative of the movement characteristics of movement of the arm of patient 12 to cloud 26, and possibly with other contextual information like location or time of day. One or more processors 28 of cloud 26 may then determine the activity patient 12 is undertaking. Insulin pump 14 may then deliver insulin based on the determined activity of patient 12.

One example way in which one or more processors 28 may be configured to determine that patient 12 is undertaking an activity and determine therapy to deliver is described in U.S. Patent Publication No. 2020/0135320 A1. In general, one or more processors 28 may first go through an initial "learning" phase, in which one or more processors 28 receive information to determine behavior patterns of patient 12. Some of this information may be provided by patient 12. For example, patient 12 may be prompted or may himself/herself enter information into patient device 24 indicating that patient 12 is undertaking a particular activity, the length of the activity, and other such information that one or more processors 28 can utilize to predict behavior of patient 12. After the initial learning phase, one or more processors 28 may still update the behavior patterns based on more recent received information, but require fewer to no information from patient 12.

In the initial learning phase, patient 12 may provide information about the dominant hand of patient 12 (e.g., right or left-handed) and where patient 12 wears wearable device 22 (e.g., around the wrist of right hand or left hand). Patient 12 may be instructed to wear wearable device 22 on the wrist of the hand patient 12 uses to eat. Patient 12 may also provide information about the orientation of wearable device 22 (e.g., face of wearable device 22 is on the top of the wrist or bottom of the wrist).

In the initial learning phase, patient 12 may enter, proactively or in response to prompt/query, information (e.g., through patient device 24) indicating that patient 12 is consuming a meal. During this time, wearable device 22 may continuously determine the one or more movement characteristics (e.g., gestures) and/or posture of patient 12, and output such information to patient device 24 that relays the information to one or more processors 28. One or more processors 28 may store information of the one or more movement characteristics of movement of the arm of patient 12 during the eating to later determine whether patient 12 is eating (e.g., whether the received information of the manner and frequency of movement of the arm of patient 12 aligns with the stored information of the manner and frequency of movement of the arm of patient 12 when patient 12 was known to be eating).

The above describes arm movement as a factor in determining whether patient 12 is eating. However, there may be various other factors that can be used separately or in combination with arm movement to determine whether patient 12 is eating. As one example, patient 12 may eat at regular time intervals. As another example, patient 12 may eat at certain locations. In the initial learning phase, when patient 12 enters that he or she is eating (e.g., through patient device 24), patient device 24 may output information about the time of day and the location of patient 12. For example, patient device 24 may be equipped with a positioning device, such as global positioning system (GPS) unit, and patient device 24 may output location information determined by the GPS unit. There may be other ways to determine location such as based on Wi-Fi connection and/or access to 4G/5G LTE, or some other form of access, such as based on telecom database tracking device location of patient device 24. Time of day and location are two examples of contextual information that can be used to determine whether patient 12 is eating.

However, there may be other examples of contextual information for patient 12 such as sleep pattern, body temperature, stress level (e.g., based on pulse and respiration), heart rate, etc. In general, there may be various biometric sensors (e.g., to measure temperature, pulse/heart rate, breathing rate, etc.), which may be part of wearable device 22 or may be separate sensors. In some examples, the biometric sensors may be part of sensor 20.

The contextual information for patient 12 may include conditional information. For example, patient 12 may eat every 3 hours, but the exact times of when patient 12 eats may be different. In some examples, the conditional information may be a determination of whether patient 12 has eaten and if a certain amount of time (e.g., 3 hours) has passed since patient 12 ate. In general, any information that establishes a pattern of behavior may be utilized to determine whether patient 12 is eating.

One or more processors 28 may utilize artificial intelligence, such as machine-learning or other data analytics techniques, based on the information determined by and/or collected by wearable device 22 and patient device 24 to determine whether patient 12 is eating. As one example, during the initial learning phase, one or more processors 28 may utilize neural network techniques. For example, one or more processors 28 may receive training data from patient 12 that is used to train a classifier module executing on one or more processors 28. As described above, one or more processors 28 may receive the training data based on patient confirmation when patient device 24 and/or wearable device 22 determine, based on manner and frequency of movement of the arm of patient 12, that patient 12 is eating (e.g., a gesture that aligns with movement of arm for eating). One or more processors 28 may generate and store a labeled data record that includes the features related to the movement, along with other contextual features, such as time of day or location. One or more processors 28 may train the classifier on a labeled dataset that includes multiple labeled data records, and one or more processors 28 may use the trained classifier model to more accurately detect the start of a food intake event.

Other examples that may be used for neural networks include behavior patterns. For example, patient 12 may only eat a particular food after exercising, and always eats that particular food after exercising. Patient 12 may eat at a particular time and/or place. There may be various conditions that together indicate a pattern in behavior of patient 12.

As another example, one or more processors 28 may utilize k-means clustering techniques to determine whether patient 12 is eating. For example, during the initial learning phase one or more processors 28 may receive different types of contextual information and form clusters, where each cluster represents a behavior of patient 12 (e.g., eating, sleeping, walking, exercising, etc.). For example, patient 12 may enter information (e.g., into patient device 24) indicating that he or she is walking. One or more processors 28 may utilize all the contextual information received when patient 12 is walking to form a first cluster associated with walking. Patient 12 may enter information (e.g., into patient device 24) indicating that he or she is eating. One or more processors 28 may utilize all the contextual information received when patient 12 is eating to form a second cluster associated with eating, and so on. Then, based on received contextual information, one or more processors 28 may determine which cluster aligns with the contextual information, and determine the activity patient 12 is undertaking. As described in more detail, the type of activity, and a prediction of when the activity will occur, may be utilized to determine when to delivery insulin therapy. There may be other examples of machine learning, and the example techniques are limited to any particular machine learning technique.

There may be various other ways in which one or more processors 28 may determine the activity patient 12 is undertaking. This disclosure provides some example techniques for determining the activity patient 12 is undertaking, but the example techniques should not be considered limiting.

During the initial learning phase, patient 12 may also enter information about the activity that patient 12 is undertaking. For example, with eating, patient 12 may enter information indicating what patient 12 is eating and/or how many carbohydrates there are in the food that patient 12 is eating. As one example, at 9:00 every morning, patient 12 may enter that he or she is having a bagel or enter that the patient 12 is consuming 48 grams of carbohydrates.

In some examples, one or more processors 28 may be configured to determine an amount of insulin (e.g., therapy dosage of bolus insulin) to deliver to patient 12. As one example, memory accessible by one or more processors 28 may store patient parameters of patient 12 (e.g., weight, height, etc.). The memory may also store a look-up table that indicates an amount of bolus insulin that is to be delivered for different patient parameters and different types of foods. One or more processors 28 may access the memory and based on the type of food patient 12 is eating and patient parameters may determine the amount of bolus insulin that patient 12 is to receive.

Accordingly, in one or more examples, one or more processors 28 may utilize information about the movement characteristics of movement of arm, eating pace, quantity of food consumption, food content, etc., while also tracking other contextual information. Examples of the contextual information include location information, time of day, wake up time, amount of time since last eaten, calendar event, information about person patient 12 may be meeting, etc. One or more processors 28 may identify patterns and correlations between all these various factors to determine an activity patient 12 undertaking, like eating.

After the initial learning phase, one or more processors 28 may automatically, and with minimal input from patient 12, determine that patient 12 is undertaking a particular activity, like eating, and determine an amount of bolus insulin to deliver based on the determination. One or more processors 28 may output the recommendation of the amount of bolus insulin to deliver to patient device 24. Patient device 24, may then in turn, control insulin pump 14 to deliver the determined amount of insulin. As one example, patient device 24 may output to insulin pump 14 the amount of bolus insulin to deliver with or without user confirmation. As another example, patient device 24 may output a target glucose level, and insulin pump 14 may deliver the insulin to achieve the target glucose level. In some examples, it may be possible for one or more processors 28 to output to patient device 24 information indicative of the target glucose level, and patient device 24 may output that information to insulin pump 16. All of these examples may be considered as examples of one or more processors 28 determining an amount of insulin to deliver to patient 12.

The above describes example ways in which to determine if patient 12 is undertaking an activity, determining an amount of insulin to deliver, and causing the amount of insulin to be delivered. The example techniques may require little to no intervention from patient 12. In this manner, there is an increase in likelihood that patient 12 will receive the correct amount of dosage of insulin at the right time, and decrease in likelihood of human error causing issues (e.g., patient 12 forgetting to log meals, forgetting to take insulin, or taking insulin but forgetting to have taken insulin).

While the above example techniques may be beneficial in patient 12 receiving insulin at the right time, this disclosure describes example techniques to further proactively deliver insulin to patient 12. As described above, patient 12 may experience an increase in glucose level after a meal, referred to as postprandial (i.e., after meal) glucose level. This disclosure describes example techniques that may further limit the increase in the postprandial glucose level, as one example, but the example techniques are applicable for other times when there may be change in glucose level.

In one or more examples, utilizing the above techniques, rather than determining when patient 12 is eating, one or more processors 28 may be configured to determine (e.g., predict) that patient 12 is going to eat (e.g., a meal event is to occur). For example, one or more processors 28 may utilize the contextual information such as time of day, location, sleep pattern, etc., and based on behavior patterns of patient 12, determine (e.g., predict) that a meal event is to occur before the meal event actually occurs. One or more processors 28 may also determine type of food and/or amount of carbohydrates patient 12 is to consume during the meal event. For instance, as described above, patient 12 may consume 48 grams of carbohydrates as part of breakfast every day at 9:00 am. Based on the behavior pattern, time of day, and location, one or more processors may determine that patient 12 is going to consume 48 grams of carbohydrates at 9:00 am.

In accordance with one or more example techniques described in this disclosure, one or more processors 28 may determine that a meal event is to occur. One or more processors 28 may receive contextual information that one or more processors 28 use to determine that the meal event is to occur. As an example, one or more processors 28 may receive information indicative of at least one of time of day or location of patient 12, and determine that the meal event is to occur based on the received information.

In response to the determination indicating that the meal event is to occur, one or more processors 28 may output instructions to insulin pump 14 (e.g., through patient device 24) to deliver a partial therapy dosage prior to the meal event. For example, one or more processors 28 may determine the amount of bolus insulin patient 12 is to receive, as described above (e.g., based on patient behavior and pattern). One or more processors 28 may determine a portion of the amount of bolus insulin patient 12 is to receive, and insulin pump 14 may deliver that the determined portion.

In one or more examples, prior to the meal event may be a time before movement characteristics indicate that patient 12 is eating. That is, one or more movement characteristics of patient 12 may not indicate that patient 12 is eating or is starting to eat. However, other contextual information such as time of day and location may indicate that patient 12 is going to be eating. One or more processors 28 may be configured to output instructions to insulin pump 14 to deliver the partial therapy dosage before movement characteristics of patient 12 indicate that patient 12 is eating or is just starting to eat. The amount of time prior to the meal event when one or more processors 28 output instructions to insulin pump 14 may be immediately before start of meal, 1 hour to immediately before predicted start of meal, 1 hour to 30 minutes before predicted start of meal, 30 minutes to before predicted start of meal, and preferably 15 minutes to predicted start of meal, such as 30 minutes to 15 minutes before predicted start of meal, or less than 15 minutes before predicted start of meal.

In general, patient 12 may receive the partial therapy dosage about 15 minutes before a meal. This is generally good for meals with a balance of carbohydrates, protein, and fat. If patient 12 is predicted to consume a high fat meal, patient 12 may receive the partial therapy dosage closer to the meal event occurring, and receive the remaining therapy dosage after an hour or so. However, very rapid acting carbohydrates, such as in apple juice, patient 12 may receive the partial therapy dosage more than 15 minutes before the meal and still reduce postprandial glucose levels.

Accordingly, in one or more examples, the type of meal that patient 12 is predicted to consume may impact when patient 12 is to receive the partial therapy dosage. For example, if patient 12 is predicted to eat a balanced meal of carbohydrates, protein, and fat, then patient 12 may receive the partial therapy dosage at least a first period of time (e.g., 15 minutes) before the meal. If patient 12 is predicted to eat a high fat or protein and low carbohydrate meal, then patient 12 may receive the partial therapy dosage a second period of time, less than the first period of time, (e.g., approximately 5 minutes or less than 5 minutes) before the meal. If patient 12 is precited to eat a high carbohydrate meal that is low in fat or protein, then patient 12 may receive the partial therapy dosage more than the first period of time (e.g., 15 minutes) before the meal. In general, delivery of the partial therapy dosage before the meal provides reduction in postprandial glucose levels regardless of the carbohydrate, fat, and protein content of the meal.

For example, one or more processors 28 may determine that patient 12 is consuming a meal or is to consume a meal (e.g., a meal event is occurring or a meal event is to occur), and then determine a recommendation for the best time, dosage, and/or settings for the insulin for patient 12 based on historical trend (e.g., patient behavior and pattern) and/or based on physiological model in order to optimize glucose control for patient 12. For example, one or more processors 28 may determine amount of the partial therapy dosage and the time to take the partial therapy dosage based on the physiological model.

An example of a physiological model is a "digital twin." One or more processors 28 may be configured to utilize a "digital twin" of patient 12 to determine an amount of bolus insulin patient 12 is to receive. A digital twin may be a digital replica or model of patient 12. The digital twin may be software executing on one or more processors 28. The digital twin may receive, as input, information about what patient 12 ate. Because the digital twin is a digital replica of patient 12, the output from the digital twin may be information about what the glucose level of patient 12 may be after eating, as well as a recommendation of how much bolus insulin to deliver to patient 12 to control the increase the glucose level.

For example, the digital twin may indicate what the correct dose should have been for a meal that patient 12 ate in the past. In one or more examples, patient 12 may enter information indicative of food patient 12 ate and one or more processors 28 may receive information about glucose levels. Utilizing information indicative of food that patient 12 ate and glucose levels, one or more processors 28 may utilize the digital twin to determine what the insulin dose should have been (e.g., based on how the digital twin models how the food will affect the patient's glucose levels). Then, at a subsequent time when patient 12 is predicted to eat the same meal, one or more processors 28 may determine what the insulin dose should be based on insulin dose amount that the digital twin had previously determined.

In this example, the determined portion of the amount of bolus insulin is a partial therapy dosage that insulin pump 14 may deliver prior to the meal event (e.g., prior to eating). For example, the partial therapy dosage may be in range of 1% to 5%, 1% to 9%, 10% to 19%, 20% to 29%, 30% to 39%, or 40% to 50%. It may be possible for the partial therapy dosage to be more than 50% of the amount of bolus insulin that is to be delivered for a given meal event, but in some examples, the partial therapy dosage is less than 50% of the amount of insulin that is to be delivered. As an example, if X grams of bolus insulin is to be delivered to patient 12 based the amount of carbohydrates patient 12 is to consume at the meal event (e.g., as determined by one or more processors 28), then insulin pump 14 may deliver Y grams of bolus insulin, where Y is less than 0.5*X.

In some examples, the value of Y may be based on the amount of carbohydrates, protein, and/or fat predicted to be in the meal. For example, if patient 12, based on patient behavior pattern, is predicted to eat a high fat meal, then the value of Y may be less than the value of Y where patient 12, based on patient behavior pattern, is predicted to eat a high carbohydrate meal that is low in fat, protein, or fiber (e.g., quick carb meals like juices).

In some examples, the value of Y may be fixed value regardless of carbohydrate content of meal. The value of Y may be based on the patient's age and body weight. In examples where the value of Y is fixed, there is a reduction in risk of hypoglycemia if the prediction is incorrect on the amount of carbohydrates, fat, protein, or fiber in a meal.

By delivering a partial therapy dosage, the postprandial glucose level may not increase as much or may increase more slowly so that there is not a spike in the glucose level of patient 12 due to the meal consumption. Also, because insulin pump 14 may deliver a partial therapy dosage rather than the full amount of the therapy dosage, in case patient 12 does not consume food (e.g., there is no meal event), the glucose level of patient 12 may not drop too low, and the chances of patient 12 experience impact from low glucose level may be minimized.

In some examples, one or more processors 28 may cause patient device 24 and/or wearable device 22 to output a notification confirming whether patient 12 is going to eat. If patient 12 indicates via wearable device 22 or patient device 24 that he or she will not eat, then one or more processors 28 may not output instructions to cause insulin pump 14 to deliver the partial therapy dosage. Such a notification confirming whether patient 12 is going to eat is not necessary in all examples.

One or more processors 28 may then determine that the meal event is occurring based on frequency and manner of movement of an arm of patient 12. For example, one or more processors of wearable device 22 may be configured to determine one or more movement characteristics (e.g., detect gesture movement, as described above) by patient 12. One or more processors 28 may receive information indicative of the gesture movement (e.g., one or more movement characteristics), and determine whether the gesture movement aligns with movement of patient 12 eating. If the gesture movement aligns with movement of patient 12 eating, one or more processors 28 may determine that patient 12 is indeed eating (i.e., determine that the meal event is occurring).

In response to determining that the meal event is occurring, one or more processors 28 may output instructions to insulin pump 14 (e.g., via patient device 22) to deliver a remaining therapy dosage with or without user confirmation. One or more processors 28 may output instructions to deliver the remaining therapy dosage while patient 12 is eating or after patient 12 has completed eating (e.g., based on lack of movement of the arm of patient 12 or movement that no longer aligns with patient 12 eating). The remaining therapy dosage may be Z grams of bolus insulin, where Z is approximately equal to X−Y. For example, if Y is equal to 0.2*X, then Z is equal to 0.8*X.

There may be various ways in which to determine if patient 12 has completed eating. As one example, the movement characteristics of the arm of patient 12 may indicate that patient 12 is no longer eating. Also, in some examples, one or more processors 28 may have, during the initial learning phase, determined an amount of time that patient 12 generally eats or an amount of bites that patient 12 generally takes to eat a meal. One or more processors 28 may utilize such information to determine whether patient 12 completed eating.

As described above, in some examples, the partial therapy dosage is less than half of the amount of therapy dosage (e.g., Y is less than 0.5*X). Accordingly, an amount of insulin for the partial therapy dosage may be less than an amount of insulin for the remaining therapy dosage (e.g. Y<Z).

In the above example, one or more processors 28 may determine how much bolus insulin that insulin pump 14 is to deliver (e.g., determine an amount of therapy dosage), and then determine the amount of the partial therapy dosage. However, the example techniques are not so limited. In some examples, rather than or in addition to determining the amount of therapy dosage, one or more processors 28 may output instructions for insulin pump 14 to deliver a set amount for the partial therapy dosage based on determination that a meal event is to occur. Then, in response to the meal event occurring, one or more processors 28 may deliver the remaining therapy dosage based on type of meal that patient 12 consumed or based on current glucose level (e.g., as determined by sensor 20).

In the example where one or more processors 28 determine an amount of insulin that is to be delivered to the patient to accommodate the consumption of the meal or where one or more processors 28 output instructions to insulin pump 14 to deliver the partial therapy dosage, the partial therapy dosage may be a portion of an amount of insulin that is to be delivered to the patient to accommodate the consumption of the meal. The remaining therapy dosage may be a remaining portion of the amount of insulin the patient that is to be delivered to the patient to accommodate the consumption of the meal (e.g., after the meal or during the meal such as mid-point of the meal based on prediction of when patient 12 will complete eating).

There may be various examples of the instructions that one or more processors 28 output to cause insulin pump 14 to deliver the therapy dosage. As one example, one or more processors 28 may output instructions that specify the amount of therapy dosage to deliver. As another example, one or more processors 28 may output instructions that specify a target glucose level. In response to the specified target glucose level, insulin pump 14 may deliver bolus insulin to achieve the target glucose level based on feedback from sensor 20 of the current glucose level. In each of these examples, one or more processors 28 may be considered as outputting instructions to insulin pump 14 to cause insulin pump 14 to deliver a partial therapy dosage prior to the meal event or to deliver a remaining therapy dosage (e.g., during the meal event or after the meal event).

The above described the example techniques with respect to one or more processors 28. However, the example techniques are not so limited. The example techniques may be performed by one or more processors of patient device 24. The example techniques may be performed by one or more processors of wearable device 22. The example techniques may be performed by one or more processors of insulin pump 14. In some examples, any combination of one or more processors 28, one or more processors of patient device 24, one or more processors of wearable device 22, or one or more processors of insulin pump 14 may be configured to perform the example techniques described in this disclosure.

As one example, one or more processors 28 may be a first set of processors. A second set of processors may be the one or more processors of wearable device 22 worn by patient 12. To determine that the meal event is occurring, the second set of processors may be configured to detect one or more movement characteristics of patient 12. At least one of the first set of processors or the second set of processors may be configured to determine that the meal event is occurring based on the movement characteristics. As another example, the second set of processors of wearable device 22 may output information indicative of the movement characteristics to a third set of processors of patient device 24, and the third set of processors may be configured to determine that the meal event is occurring based on the gesture movement.

For ease of description, the example techniques are described with respect to one or more processors 28. However, the example techniques should not be considered limited to one or more processors. For instance, the one or more processors configured to perform the example techniques described in this disclosure may be one or more processors 28, one or more processors of patient device 24, one or more processors of wearable device 22, one or more processors of insulin pump 14, or any combination thereof.

Figure 2:
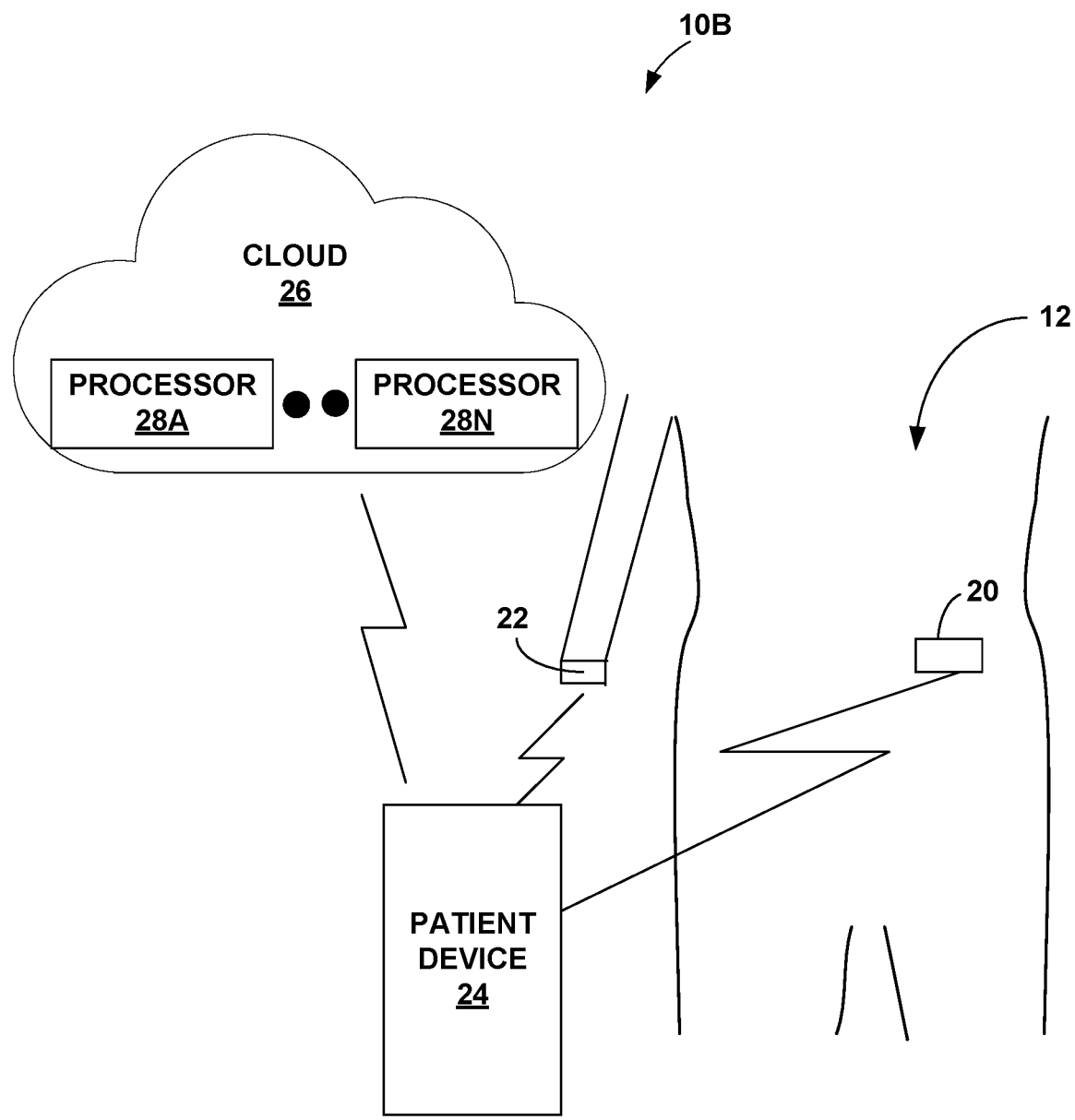
FIG. 2 is a block diagram illustrating another example system for delivering or guiding therapy dosage, in accordance with one or more examples described in this disclosure.

FIG. 2 is a block diagram illustrating another example system for delivering or guiding therapy dosage, in accordance with one or more examples described in this disclosure. FIG. 2 illustrates system 10B that is similar to system 10A of FIG. 1. However, in system 10B, patient 12 may not have insulin pump 14. Rather, patient 12 may utilize a manual injection device (e.g., an insulin pen or syringe) to deliver insulin. For example, rather than insulin pump 14 automatically delivering insulin, patient 12 (or possible a caretaker of patient 12) may fill a syringe with insulin or set the dosage amount in an insulin pen and inject himself or herself.

In the example of FIG. 2, similar to FIG. 1, one or more processors 28 may determine that a meal event is to occur. In FIG. 2, in response to the determination indicating that the meal event is to occur, one or more processors 28 may output instructions to a device (e.g., patient device 24) to notify patient 12 to use the syringe or insulin pen to take the partial therapy dosage prior to the meal event occurring. The instructions to patient device 24 to notify patient 12 to use the syringe or insulin pen to take the partial therapy dosage may include a reminder and/or may specify an amount of insulin to inject. In some examples, patient device 24 may output the instructions to an insulin pen to automatically set the recommended insulin dose. One or more processors 28 may determine that the meal event is occurring based on the movement characteristics of an arm of patient 12. In response to the determination indicating that the meal event is occurring, one or more processors 28 may output instruction to the device (e.g., patient device 24) to notify patient 12 to use the syringe or insulin pen to take the remaining therapy dosage. In the example of FIG. 2, description of notifying patient 12 to use the syringe or insulin pen encompasses examples where a patient or caregiver uses the syringe insulin pen to deliver the partial therapy dosage and/or remaining therapy dosage. That is, any notification to patient 12 includes examples where a caregiver is separately notified or where the caregiver reads the notification on patient device 24 that patient 12 is to receive a therapy dosage (e.g., partial therapy dosage or remaining therapy dosage).

Figure 3:
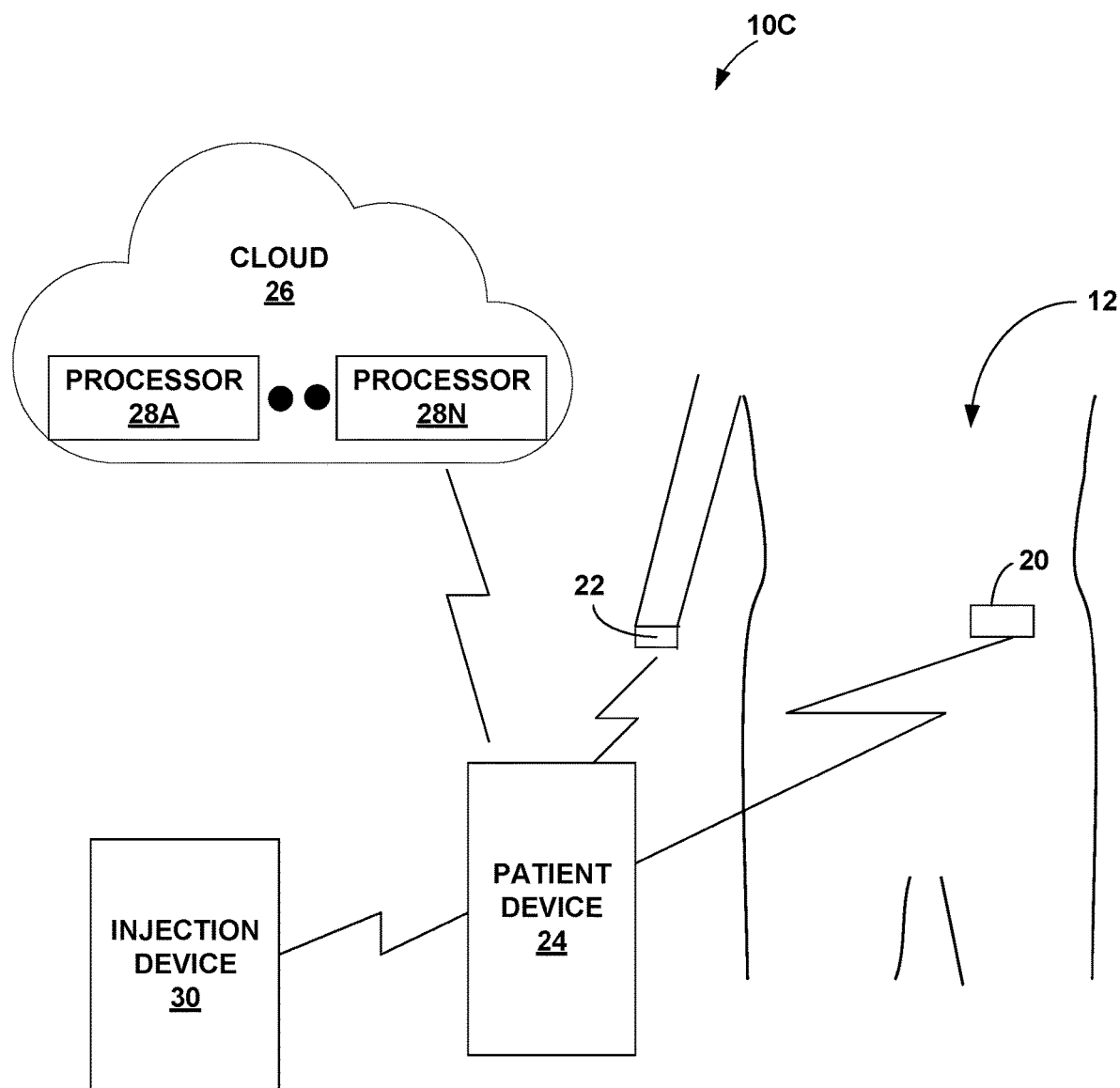
FIG. 3 is a block diagram illustrating another example system for delivering or guiding therapy dosage, in accordance with one or more examples described in this disclosure.

FIG. 3 is a block diagram illustrating another example system for delivering or guiding therapy dosage, in accordance with one or more examples described in this disclosure. FIG. 3 illustrates system 10C that is similar to system 10A of FIG. 1 and system 10B of FIG. 2. In system 10C, patient 12 may not have insulin pump 14. Rather, patient 12 may utilize injection device 30 to deliver insulin. For example, rather than insulin pump 14 automatically delivering insulin, patient 12 (or possible a caretaker of patient 12) may utilize injection device 30 to inject himself or herself.

As described above, injection device 30 may be different than a syringe or a basic insulin pen because injection device 30 may be a device that can communicate with patient device 24 and/or other devices in system 10C. Also, injection device 30 may include a reservoir, and based on information indicative of how much therapy dosage to deliver may be able to dose out that much insulin for delivery. In some examples, injection device 30 may be similar to insulin pump 14, but not worn by patient 12. One example of injection device 30 is an insulin pen, sometimes also called a smart insulin pen. Another example of injection device 30 may be an insulin pen with a smart cap, where the smart cap can be used to set particular doses of insulin.

In the example of FIG. 3, similar to FIG. 1, one or more processors 28 may determine that a meal event is to occur. In FIG. 3, in response to the determination indicating that the meal event is to occur, one or more processors 28 may output instructions to a device (e.g., patient device 24) to notify patient 12 to use injection device 30 to take the partial therapy dosage prior to the meal event occurring. Patient device 24 may output information to injection device 30 indicating the amount for the partial therapy dosage so that injection device 30 can prepare the correct amount of insulin for delivery with little to no intervention from patient 12 (e.g., injection device 30 may automatically set the amount of insulin based on the information received from patient device 24). In this way, in response to the prediction indicating that the meal event is to occur, one or more processors 28 may output instructions to injection device 30 to cause injection device 30 to prepare the partial therapy dosage (e.g., load in the amount of insulin needed so that patient 12 can inject himself/herself with the partial therapy dosage).

One or more processors 28 may determine that the meal event is occurring based on movement characteristics of movement of an arm of the patient. In response to the determination indicating that the meal event is occurring, one or more processors 28 may output instructions to the device (e.g., patient device 24) to notify patient 12 to use injection device 30 to take the remaining therapy dosage. Patient device 24 may output information to injection device 30 indicating the amount for the remaining therapy dosage so that injection device 30 can prepare the correct amount of insulin for delivery with little to no intervention from patient 12 (e.g., injection device 30 may automatically set the amount of insulin based on the information received from patient device 24). In this way, in response to the determination indicating that the meal event is occurring, one or more processors 28 may output instructions to injection device 30 to cause injection device 30 to prepare the remaining therapy dosage (e.g., load in the amount of insulin needed so that patient 12 can inject himself/herself with the remaining therapy dosage).

Similar to FIG. 2, in the example of FIG. 3, description of notifying patient 12 to use injection device 30 encompasses examples where a caregiver uses injection device 30 to deliver the partial therapy dosage and/or remaining therapy dosage. That is, any notification to patient 12 includes examples where a caregiver is separately notified or where the caregiver reads the notification on patient device 24 that patient 12 is to receive a therapy dosage (e.g., partial therapy dosage or remaining therapy dosage).

In the example of FIGS. 2 and 3, one or more processors 28 may determine when a meal event is to occur, and determine (e.g., based on information from a digital twin) the amount of the partial therapy dosage and/or remaining therapy dosage based on when the meal event is to occur and behavior pattern data indicative of type of food patient 12 is going to consume. One or more processors 28 may also determine the time to take the partial therapy dosage and/or remaining therapy dosage. One or more processors 28 may output instructions to patient device 24 to notify patient 12 about the amount of therapy dosage and timing for delivering the therapy dosage. In the example of FIG. 3, patient device 24 may further output information of the amount of therapy dosage and timing for delivering the therapy dosage to injection device 30.

After patient 12 takes the insulin from the syringe or injection device 30 based on the notification, patient 12 may log into patient device 24 that he or she took the therapy dosage. One or more processors 28 may confirm that the meal event actually occurred based on gesture movement (e.g., one or more movement characteristics indicating that patient 12 is no not moving arms in way that aligns with meal), and then output a notification to patient 12 via patient device 24 to take the remaining therapy dosage. As described above, there may be various ways in which to determine when patient 12 completed the meal. In any of the examples of FIGS. 1-3, if patient 12 stopped eating earlier than anticipated (e.g., based on patient 12 no longer moving arm in manner or frequency indicative of eating), one or more processors 28 may output a notification via patient device 24 asking patient 12 to eat more to avoid effects of hypoglycemia. If patient 12 keeps eating beyond an anticipated time (e.g., based on patient 12 moving arm in manner or frequency indicative of eating), one or more processors 28 may output a notification via patient device 24 to ask patient 12 to take more insulin. In the example of FIG. 1, one or more processors 28 may cause insulin pump 14 to deliver more insulin, with or without notifying patient 12, by lowering the target glucose level and/or by instructing insulin pump 14 to deliver more insulin.

The above examples described insulin pump 14, a syringe, and injection device 30 as example ways in which to deliver insulin. In this disclosure, the term "insulin delivery device" may generally refer to any device used to deliver insulin. Examples of insulin delivery device include insulin pump 14, a syringe, and injection device 30. As described, the syringe may be a device used to inject insulin but is not necessarily capable of communicating or dosing a particular amount of insulin. Injection device 30, however, may be a device used to inject insulin that may be capable of communicating with other devices (e.g., via Bluetooth, BLE, and/or Wi-Fi) or may be capable of dosing a particular amount of insulin. Injection device 30 may be powered (e.g., battery powered) device, and the syringe may be device that requires no power.

Because there may be different ways in which to deliver insulin, in one or more examples, in response to the determination indicating that the meal event is to occur, one or more processors 28 may output instructions to at least one of: (1) the insulin delivery device (e.g., insulin pump 14) to cause the insulin delivery device to deliver a partial therapy dosage prior to the meal event occurring, (2) to a device (e.g., patient device 24) to notify the patient to use the insulin delivery device (e.g., syringe or injection device 30) to take the partial therapy dosage prior to the meal event occurring, or (3) to the insulin delivery device (e.g., injection device 30) to cause the insulin delivery device to prepare the partial therapy dosage (e.g., preload the determined amount of insulin so that patient 12 can deliver the partial therapy dosage) prior to the meal event occurring. Also, in response to the determination indicating that the meal event is occurring, one or more processors 28 may output instructions to at least one of: (1) the insulin delivery device (e.g., insulin pump 14) to deliver a remaining therapy dosage, (2) to the device (e.g., patient device 24) to notify the patient to use the insulin delivery device (e.g., syringe or injection device 30) to take the remaining therapy dosage, or (3) to the insulin delivery device (e.g., injection device 30) to cause the insulin delivery device to prepare the remaining therapy dosage. Although described with respect to one or more processors 28, the example techniques may be performed by one or more processors 28, one or more processors of patient device 24, one or more processors of wearable device 22, one or more processors of insulin pump 14, or any combination thereof.

Accordingly, FIGS. 1-3 illustrate examples in which wearable device 22 worn on a wrist of patient 12 can be used to detect a meal event occurring (e.g., patient 12 eating). Wearable device 22 may include six-axis inertial measurement unit which includes accelerometers and gyroscopes. Systems 10A-10C include one or more processors 28 that may be configured to determine meal dosing of insulin (e.g., how much insulin to deliver to patient 12 to accommodate consumption of the meal). One or more processors 28 may also be configured to detect consumption of food via eating or drinking based on one or more movement characteristics such as gesture movement (e.g., manner and frequency of movement of arm of patient 12).

One or more processors 28, wearable device 22, and/or patient device 24 may detect when food is being consumed by patient 12. One or more processors 28, wearable device 22, and/or patient device 24 may determine an amount of insulin to be delivered to accommodate the meal (e.g., the amount of insulin that is needed to counteract the increase in glucose level due to consuming the meal), and communicate with insulin pump 14, wearable device 22, and/or patient device 24 information indicative of the amount of insulin to be delivered. In some examples, the amount of insulin may be predetermined or fixed, in which case information indicative of the amount of insulin may or may not need to be communicated. Patient device 24, wearable device 22, and/or insulin pump 14 may output notification of the amount of insulin that is to be delivered, and may also provide reminder to patient 12 for the insulin (e.g., such as in examples of FIGS. 2 and 3, where there is no insulin pump 14). In some examples, patient device 24 may output to injection device 30 information indicative of the amount of insulin that is to be delivered.

In accordance with one or more examples described in this disclosure, rather than waiting to deliver the entire insulin (e.g., bolus insulin) after the meal event or before the meal event, patient 12 may receive a portion of the insulin (e.g., partial therapy dosage) prior to the meal event occurring to reduce the postprandial increase the glucose level but with a low enough dosage to reduce any negative impact in case patient 12 chooses not to eat. As described above, prior to the meal event may be prior to one or more movements characteristics indicating that patient 12 is eating or starting to eat, and may be some amount of time prior to the meal event or imminent start of the meal event. Patient 12 may then receive the remaining therapy dosage after there is confirmation that patient 12 is actually eating (i.e., the meal event is occurring) based on movement characteristics or prediction of how long meal will take, etc. The following describes some example ways of utilizing the techniques described in this disclosure.

As described above, based on manual logging of food entry and data uploaded to one or more processors 28 in cloud 26, one or more processors 28 may determine a pattern of meal behavior. For instance, one or more processors 28 may utilize machine learning (e.g., updating classifiers or k-means clustering, as two examples) to determine patterns for timing of eating for patient 12. Also, one or more processors 28 may determine patterns in amount of carbohydrates patient 12 consumes.

Once the eating pattern for timing and possible amount of carbohydrates is determined (e.g., as part of the initial learning phase), in response to the determination indicating that the meal event is to occur, one or more processors 28 may determine an amount of partial therapy dosage and timing of delivering the partial therapy dosage and output instructions to the insulin delivery device (e.g., insulin pump 14) to cause the insulin delivery device (e.g., automatically or with minimal user intervention) to deliver the partial therapy dosage prior to the meal event. As one example of the instructions to insulin pump 14, one or more processors 28 may output instructions to insulin pump 14 (e.g., via patient device 24) to lower a glucose target before the meal is consume, which in turn causes insulin pump 14 to deliver the bolus insulin to try, with or without patient confirmation at insulin pump 14, and achieve the lower glucose target. One or more processors 28, insulin pump 14, and/or patient device 24 may determine an insulin amount that is safe for patient 12 in order to increase active insulin (i.e., bolus insulin) without increasing the risk of hypoglycemia. This way, the postprandial high glucose level may be reduced by delivering insulin sooner into patient 12.

One or more processors 28 may determine that the meal event is occurring based on one or more movement characteristic of movement of an arm of patient 12 (e.g., based on gesture movement detected by wearable device 22) to confirm that patient 12 is actually eating. In response to the determination indicating that the meal event is occurring, one or more processors 28 may output instructions to insulin pump 14 (e.g., via patient device 24) to deliver a remaining therapy dosage. Insulin pump 14 may deliver the remaining therapy dosage (e.g., either during the meal or after confirmation that the meal ended based on wearable device 22 no longer detecting movement indicative of eating).

For example, at noon, patient 12 may typically eat a sandwich consisting of 55 grams of carbohydrates. One or more processors 28 may output instructions to insulin pump 14 to cause insulin pump 14 to lower the glucose target 20 minutes prior to the typical meal being consumed (e.g., to deliver a partial therapy dosage). At noon, one or more processors 28 may determine a meal is being eaten (e.g., the meal event is occurring based on movement characteristics of arm of patient 12) and may output instructions to insulin pump 14. Insulin pump 14 may deliver the remaining therapy dosage during the meal or after the meal is consumed.

In the above example, one or more processors 28 outputted instructions to lower the target glucose level as a way to deliver a partial therapy dosage prior to the meal event occurring. In some examples, one or more processors 28 may output instructions that define the amount of partial therapy dosage to deliver (e.g., including a number of fixed units of insulin to deliver) prior to the meal event occurring. For example, as above, patient 12 may consume a sandwich at noon consisting of 55 grams of carbohydrates. One or more processors may output instructions to insulin pump 14 to deliver a small pre-meal amount of bolus insulin prior to the typical meal being consumed.

The above examples described time of day (e.g., noon) as being a factor in determining when and whether to deliver the partial therapy dosage prior to a meal event. In some examples, one or more processors 28 may utilize location information (e.g., instead of time of day or in combination with time of day). For example, one or more processors 28 may utilize machine learning to determine patterns and correlating types of foods and/or amount of food to location where food is purchased or consumed. Once a pattern of meal behavior for timing and location is determined by one or more processors 28 (e.g., as part of the initial learning phase), one or more processors 28 may output instructions that cause insulin pump 14 to deliver an amount of insulin (e.g., partial therapy dosage) that will not cause hypoglycemia before the meal is consumed. As described, in some examples, one or more processors 28 may cause patient device 24 and/or wearable device 22 to output a notification requesting confirmation that patient 12 will eat. One or more processors 28 may cause patient device 24 and/or wearable device 22 output such a notification based on the location of patient 12.

As one example, patient 12 may eat a bagel from the same bagel shop. If one or more processors 28 determine that patient 12 is near the bagel shop based on location of patient 12, one or more processors 28 may output instructions to deliver the partial therapy dosage before patient 12 enters the bagel shop. After one or more processors 28 determine that patient 12 is eating (e.g., after determining that the meal event is occurring), one or more processors 28 may output instructions that cause insulin pump 14 to deliver the remaining therapy dosage.

The above described example techniques based on time of day and location. In some examples, one or more processors 28 may utilize a combination of time of day, location, and other contextual information such as sleep pattern, calendar information, temperature, heart rate, etc. to determine whether and when to deliver to cause insulin pump 14 to deliver the partial therapy dosage. By utilizing multiple factors to determine whether patient 12 is going to eat and/or is eating (e.g., utilizing multi-factor meal recognition), the example techniques may more accurately determine (e.g., predict) when patient 12 is going to eat. One or more processors 28 may reduce the false positive rate of meal detection events by combining two or more detection inputs, which may allow for more aggressive partial therapy dosage in advance of meals. For example, if multiple items of contextual information (e.g., time of day and location) indicate that a meal event is to occur, then one or more processors 28 may be more certain that the meal event will occur, and may therefore provide a higher partial therapy dosage as compared to if fewer items of contextual information indicated that a meal event is to occur because it is more likely that patient 12 will eat, and there is less chance of hypoglycemia.

As one example, if only one context indicated that patient 12 is going to consume food (e.g., only one context that a meal event is to occur), then one or more processors 28 may have limited options on how and the amount of partial therapy dosage (e.g., lower auto-basal setpoint, lower auto-correction bolus target, or raise auto-basal insulin limit).

Auto-basal setpoint refers to the closed loop target glucose. For example, the closed loop auto-basal delivery rate (e.g., the rate at which insulin pump 14 continuously delivers basal insulin) is decreased when the measured glucose level is below the auto-basal setpoint. The closed loop auto-basal delivery rate is increased up to the auto-basal limit when the measured glucose is above the auto-basal setpoint. Auto-correction bolus target refers to the glucose target for correction boluses. The basic correction bolus equation is (current glucose−correction target)/correction factor−active insulin. The lower the correction target, the larger the correction bolus will be for a given current glucose value. Auto-basal limit refers to the maximum basal rate that is permitted to be commanded by a closed loop auto-basal controller. This is a safety feature intended to prevent over delivery of insulin due to time delays in measurements from sensor 20 and possible sensor errors. Temporarily raising this limit may provide more effective control if a meal is consumed.

However, if multiple contexts (e.g., multiple items of contextual information) indicated that patient 12 is going to consume food (e.g., multiple items of contextual information indicate that a meal event is to occur), then one or more processor 28 may perform any one of lower auto-basal setpoint, lower auto-correction bolus target, or raise auto-basal insulin limit and output instructions that cause insulin pump 14 to deliver a fixed pre-meal bolus equivalent for a small meal (e.g., for a meal that is 30 grams of carbohydrates).

In general, if only a few (e.g., one or two) items of the contextual information indicated that a meal event is to occur (e.g., there is low confidence that a meal event is to occur), then one or more processors 28 may determine a first amount of partial therapy dosage to deliver. However, if more than a few items of the contextual information indicated that a meal event is to occur (e.g., there is high confidence that a meal event is to occur), then the one or more processors may determine a second amount of partial therapy dosage to deliver. For example, the machine learning algorithms may be configured to generate a confidence value indicative of the confidence that patient 12 is to consume a meal based on the learning of patient behavior. The second amount of partial therapy dosage may be bigger than the first amount of partial therapy dosage. For example, the second amount of partial therapy dosage may be a preselected amount, whereas the first amount of partial therapy dosage may be determined based on an assumption of how many carbohydrates patient 12 is to consume. In this way, the more confidence there is that patient 12 will be consuming a meal, the more aggressive the insulin therapy can be (i.e., the greater amount of insulin prior to the meal can be delivered).

Also, the above example techniques are described with respect to insulin pump 14. However, the example techniques are extendable to examples where patient 12 does not have an automatic insulin delivery (AID) device like insulin pump 14. In examples where patient 12 does not have insulin pump 14, and instead uses a syringe or injection device 30, patient 12 may be considered as utilizing a multiple daily injections (MDIs) insulin therapy regimen. For example, similar to above, one or more processors 28 may determine whether a meal event is to occur (e.g., based on various contexts). In response to the determination indicating that the meal event is to occur, one or more processors may output instructions to a device (e.g., patient device 24) to notify the patient to use the insulin delivery device (e.g., syringe or injection device 30) to take the partial therapy dosage prior to the meal event occurring. One or more processors 28 may determine that the meal event is occurring based on movement characteristics of an arm of patient 12. In response to the determination indicating that the meal event is occurring, one or more processors 28 may output instructions to the device (e.g., patient device 24) to notify patient 12 to use the insulin delivery device (e.g., syringe or injection device 30) to take the remaining therapy dosage.

In this way, insulin dosing guidance can be provided to patient 12 based on automatic meal detection based on gesture movement (e.g., movement characteristics). One or more processors 28 may determine the right dosage and timing based on automatic detection of meals, including determining a partial therapy dosage to take before the meal.

In addition to reducing the increase in postprandial glucose levels, there may be benefits associated with automatic meal detection and delivery of a partial therapy dosage. In some examples, patient 12 may follow normal behavior patterns, but may at times include some "tag along" food items, like desert or drink. There may be a delay between when patient 12 completed eating a meal and when there is desert or drink, which may follow the meal. In some examples, patient 12 may not account for tag along foods. With the automatic meal detection, one or more processors 28 may determine that patient 12 is eating more than he or she normally does. For instance, one or more processors 28 may determine that patient 12 is eating again shortly after the meal event. Due to the partial therapy dosage that patient 12 already took, even with tag along foods, there may be reduced chance that the glucose level will become undesirably high. Also, due to the meal detection, one or more processors 28 may output instructions to further increase the bolus insulin dosage to account for the tag along foods.

As explained, there are various types of insulin delivery devices (e.g., insulin pump 14, syringe, or injection device 30). With injection device 30, patient 12 may be requested to set the level of insulin to deliver and then use injection device 30 to deliver the insulin at set times or in anticipation of an event (e.g., a meal).

One or more processors 28 may be configured to utilize patient behavior information and meal detection to determine the amount of insulin and the timing at which to deliver the insulin. One or more processors 28 may output information to patient device 24 that indicates the amount and timing for delivering insulin. In some examples, patient device 24, without assistance from one or more processors 28, may be configured to perform such example techniques. In some examples, one or more processors 28 may utilize a physiological model (e.g., a computer model of the patient indicative of how therapy will impact the patient, such as a digital twin) to determine the amount of insulin and the timing at which to deliver the insulin.

In some cases, one or more processors 28 may determine the amount of insulin to take and timing at which to take the insulin based on a prediction of what patient 12 will eat. However, patient 12 may add on "tag along" foods, such as desert or drinks. One or more processors 28 may determine, based on movement detected by wearable device 22, whether patient 12 has already injected himself or herself with insulin using injection device 30 to ensure that patient 12 does not inject himself or herself more than once. Also, one or more processors 28 may determine whether patient 12 is having additional food not accounted for (e.g., based on additional hand movements beyond those expected for a basic meal) to adjust the amount of insulin the patient is to take.

In some examples, the operation of sensor 20 may also change based on detection that patient 12 is eating. In some cases, the glucose level of patient 12 may increase, and in some cases increase at a higher rate, during a time when patient 12 is eating, as compared to when patient 12 is not eating. Accordingly, there may be benefits in more frequently determining the glucose levels when patient 12 is eating as compared to other times so that therapy can be delivered more timely.

In one or more examples, one or more processors 28 may determine that a patient is eating or is about to eat (e.g., a meal event is occurring or is to occur). In response, one or more processors 28 may instruct sensor 20 to determine and output the glucose level at a higher rate as compared to when patient 12 is not eating or about to eat. There may be various ways in which one or more processors 28 may determine that the patient is eating or about to eat, such as those described above. Accordingly, in one or more examples, one or more processors 28 may determine that a meal event is to occur or is occurring. In response to the determination, one or more processors 28 may instruct sensor 20 to output a glucose level of patient 12 at a first rate that is higher than a second rate at which sensor 20 outputs the glucose level of patient 12 when the meal event is not to occur or is not occurring. For example, the second rate may be one glucose level measurement every five minutes, and the first rate may be one glucose level measurements every minute.

With the information being received at the higher rate during meal events, one or more processors 28 and/or insulin pump 14 may be configured to more quickly update changes to the therapy dosage (e.g., increase or decrease the amount of bolus insulin to deliver) based on sensed change in the glucose level (e.g., faster/more aggressive auto-correction bolus). Also, during times when one or more processors 28 determine that a meal event is not occurring or is not to occur, sensor 20 may be able to output the glucose level measurements at a lower rate, which increases the battery life of sensor 20 and the battery life of insulin pump 14 because the power consumption of the receiver circuitry (e.g., radio circuitry) is reduced when meals are not being consumed.

As described above, one or more processors 28 may determine a partial therapy dosage to be delivered prior to the meal event, and determine a remaining therapy dosage that may be delivered during the meal event or after the meal event. In some examples, one or more processors 28 may determine therapy that is to be delivered during the meal, such as based on when patient 12 will be biting or based on a prediction of how many carbohydrates patient 12 will consume. For instance, based on patient behavior, one or more processors 28 may predict how many carbohydrates patient 12 is to consume. In some examples, one or more processors 28 may also predict how many bites patient 12 will take to consume the food.

For example, as described above, one or more processors 28, based on patient behavior, may determine an amount of time it takes patient 12 to consume a meal. In addition, during the eating of the meal, one or more processors 28 may determine the movement characteristics, which may include information of how often patient 12 moves his or her arm to his or her mouth while eating. Each instance of patient 12 moving his or her arm to his or her mouth may be an instance of a bite (e.g., moving hand to mouth to take a bite of sandwich or pizza). In some examples, it may be possible for one or more processors 28 to determine how many bites patient 12 is to take and how many carbohydrates patient 12 is to consume. Utilizing information indicative of number of bits and amount of carbohydrates, one or more processors 28 may cause insulin delivery device (e.g., insulin pump 14) to deliver small boluses of insulin throughout the meal.

For instance, some example techniques deliver bolus insulin after completion of the meal. However, there may be benefits in delivering bolus insulin while patient 12 is eating the meal to avoid sudden increases in the glucose level of patient 12. In some examples, one or more processors 28 may determine whether patient 12 is currently eating and in response, output instructions to cause an insulin delivery device (e.g., insulin pump 14) to deliver micro-bolus insulin therapy, possibly on a per-bite basis.

As one example, wearable device 22 may detect the movement characteristics of the arm of patient 12, such as how often and when patient 12 moves his or her arm to his or her mouth during the meal event. Patient 12 moving his or her arm to his or her mouth during the meal event may be indicative of patient 12 taking a bite of food. One or more processors 28 may determine, based on movement characteristics (e.g., how fast and whether movement aligns with movement of someone's hand from a plate to mouth), that patient 12 is currently eating. In response, one or more processors 28 may cause insulin pump 14 to deliver small doses of the bolus insulin at a particular frequency. For instance, one or more processors 28 may cause insulin pump 14 to deliver small doses of the bolus insulin after every instance that one or more processors 28 determined that patient 12 took a bite (e.g., based on movement of the arm).

One or more processors 28 may be configured to predict how many bites a patient takes and how much insulin to deliver for each micro-bolus delivery. For example, based on patient behavior pattern, one or more processors 28 may determine how long the patient eats (e.g., how many bites) and the amount of carbohydrates the patient consumes. Based on the prediction of the amount of carbohydrates and number of bites, one or more processors 28 may determine the amount of micro-bolus to deliver (e.g., on a per-bite basis) and/or an overall series of micro-boluses. In some examples, one or more processors 28 may ensure that multiple consecutive arm movements, indicative of eating, are detected before causing insulin pump 14 to deliver the micro-boluses.

As an example, if patient 12 typically eats a breakfast containing 45 grams to 75 grams of carbohydrates, and typically takes 10 to 15 bites, then a conservative bite bolus may be based on the low end of carbohydrates (e.g., 45 grams) and a high end of number of bites (e.g., 15). In this example, one or more processors 28 may determine that patient 12 is going to consume 3 grams of carbohydrates per bite (e.g., 45 grams/15 bites). In this example, one or more processors 28 may determine an amount of insulin to deliver for 3 grams of carbohydrates, and in response, may cause insulin pump 14 to deliver the determined amount of insulin throughout the meal. The delivery of insulin may stop if patient 12 takes more than a threshold amount of bites for a meal or after a threshold amount of time to ensure that the glucose level of patient 12 does not become too low.

In some examples, one or more processors 28, processors on patient device 24, wearable device 22, or some combination thereof may output instructions to cause insulin pump 14 to deliver the determined amount of insulin with every detected bite or in regular intervals of time during the expected meal duration. For example, in the above example, patient 12 may consume 3 grams of carbohydrates per bite. One or more processors 28 may determine the amount of insulin to deliver to address the change in glucose level due to 3 grams of carbohydrates. Patient device 24, based on movement characteristics determined by wearable device 22, may determine that patient 12 is going to take a bite (e.g., by bringing food close to mouth). In response, patient device 24 may cause insulin pump 14 to deliver the amount of insulin determined by one or more processors 28. In some examples, rather than delivering insulin on a per bite basis, insulin pump 14 may deliver insulin during regular intervals (e.g., every 10 seconds) over the duration of the meal.

In this way, one or more processors 28, processor of patient device 24, and/or processor of wearable device 22 or combination thereof may determine an amount of carbohydrates patient 12 is to eat during the meal event and a number of bites patient 12 will take during the meal event. Based on the determination of the amount of carbohydrates patient 12 is to eat and the number of bites patient 12 will take, one or more processors 28, processor of patient device 24, and/or processor of wearable device 22 or combination thereof output instructions to cause insulin delivery device (e.g., insulin pump 14) to deliver a micro-bolus or a series of micro-boluses of insulin therapy during the meal event. In some examples, to output the instructions to cause the insulin delivery device to deliver the series of micro-boluses, one or more processors 28, processor of patient device 24, and/or processor of wearable device 22 or combination thereof may be configured to output instructions to cause the insulin delivery device (e.g., insulin pump 14) to deliver the series of micro-boluses with every detected bite or in regular intervals of time.

The above example of delivering micro-boluses is described with respect to one or more processors 28. However, the one or more processors may be one or more processors of patient device 24, insulin pump 14, wearable device 22, one or more processors 28, or any combination thereof.

Figure 4:
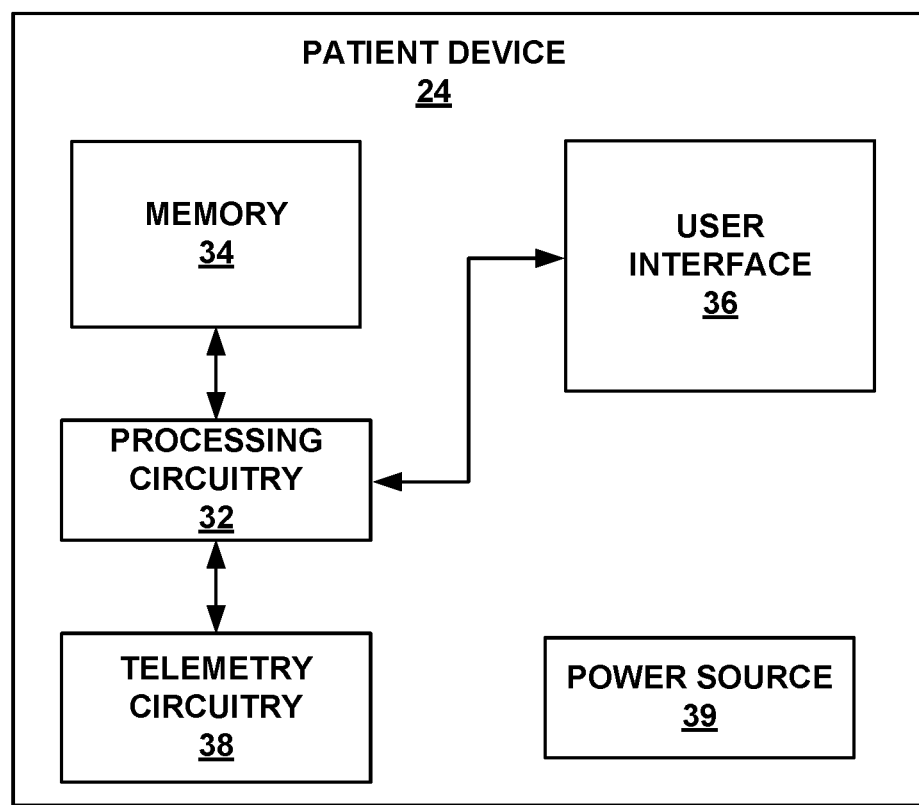
FIG. 4 is a block diagram illustrating an example of a patient device, in accordance with one or more examples described in this disclosure.

FIG. 4 is a block diagram illustrating an example of a patient device, in accordance with one or more examples described in this disclosure. While patient device 24 may generally be described as a hand-held computing device, patient device 24 may be a notebook computer, a cell phone, or a workstation, for example. In some examples, patient device 24 may be a mobile device, such as a smartphone or a tablet computer. In such examples, patient device 24 may execute an application that allows patient device 24 to perform example techniques described in this disclosure. In some examples, patient device 24 may be specialized controller for communicating with insulin pump 14.

Although the examples are described with one patient device 24, in some examples, patient device 24 may be a combination of different devices (e.g., mobile device and a controller). For instance, the mobile device may provide access to one or more processors 28 of cloud 26 through Wi-Fi or carrier network and the controller may provide access to insulin pump 14. In such examples, the mobile device and the controller may communicate with one another through Bluetooth or BLE. Various combinations of a mobile device and a controller together forming patient device 24 are possible and the example techniques should not be considered limited to any one particular configuration.

As illustrated in FIG. 4, patient device 24 may include a processing circuitry 32, memory 34, user interface 36, telemetry circuitry 38, and power source 39. Memory 34 may store program instructions that, when executed by processing circuitry 32, cause processing circuitry 32 to provide the functionality ascribed to patient device 24 throughout this disclosure.

In some examples, memory 34 of patient device 24 may store a plurality of parameters, such as amounts of insulin to deliver, target glucose level, time of delivery etc. Processing circuitry 32 (e.g., through telemetry circuitry 38) may output the parameters stored in memory 34 to insulin pump 14 or injection device 30 for delivery of insulin to patient 12. In some examples, processing circuitry 32 may execute a notification application, stored in memory 34, that outputs notifications to patient 12, such as notification to take insulin, amount of insulin, and time to take the insulin, via user interface 36.

Memory 34 may include any volatile, non-volatile, fixed, removable, magnetic, optical, or electrical media, such as RAM, ROM, hard disk, removable magnetic disk, memory cards or sticks, NVRAM, EEPROM, flash memory, and the like. Processing circuitry 32 can take the form one or more microprocessors, DSPs, ASICs, FPGAs, programmable logic circuitry, or the like, and the functions attributed to processing circuitry 32 herein may be embodied as hardware, firmware, software or any combination thereof.

User interface 36 may include a button or keypad, lights, a speaker for voice commands, and a display, such as a liquid crystal (LCD). In some examples the display may be a touchscreen. As discussed in this disclosure, processing circuitry 32 may present and receive information relating to therapy via user interface 36. For example, processing circuitry 32 may receive patient input via user interface 36. The patient input may be entered, for example, by pressing a button on a keypad, entering text, or selecting an icon from a touchscreen. The patient input may be information indicative of food that patient 12 eats, such as for the initial learning phase, whether patient 12 took the insulin (e.g., through the syringe or injection device 30), and other such information.

In some examples, processing circuitry 32 may include GPS circuitry that can identify the location of patient 12. Processing circuitry 32 may output the location of patient 12, as well as time of day information, as part of the initial learning phase to determine when and where patient 12 is eating, and then subsequently, so that one or more processors 28 can determine whether a meal event is to occur. The location and time of day are two examples of contextual information used to determine whether a meal event is to occur and/or is occurring, and the example techniques are not limited to location and time of day as being the contextual information.

In some examples, the one or more processors configured to perform the example techniques described in this disclosure may include processing circuitry 32. For example, processing circuitry 32 may be configured to determine that a meal event is to occur. Processing circuitry 32 may receive contextual information such as at least one of time of day or location of patient 12 and determine that the meal event is to occur based on the received information. In response to the determination indicating that the meal event is to occur, processing circuitry 32 may output instructions to at least one of: (1) the insulin delivery device (e.g., insulin pump 14) to cause the insulin delivery device to deliver a partial therapy dosage prior to the meal event occurring, (2) to a device (e.g., user interface 36 or injection device 30) to notify patient 12 to use the insulin delivery device (e.g., syringe or injection device 30) to take the partial therapy dosage prior to the meal event occurring, or (3) to the insulin delivery device (e.g., injection device 30) to cause the insulin delivery device to prepare the partial therapy dosage prior to the meal event occurring.

Processing circuitry 32 may determine that the meal event is occurring based on movement characteristics of movement of an arm of the patient. For example, wearable device 22 may detect gesture movement by patient 12, and processing circuitry 32 may determine that the meal event is occurring based on the gesture movement by patient 12. In response to the determination indicating that the meal event is occurring, processing circuitry 32 may output instructions to at least one of: (1) the insulin delivery device (e.g., insulin pump 14) to deliver a remaining therapy dosage, (2) to the device (e.g., user interface 36 or injection device 30) to notify patient 12 to use the insulin delivery device to take the remaining therapy dosage, or (3) to the insulin delivery device to cause the insulin delivery device to prepare the remaining therapy dosage.

As described above, in some examples, the partial therapy dosage may be a portion of an amount of insulin that is to be delivered to patient 12 to accommodate the consumption of the meal, and the remaining therapy dosage may be a remaining portion of the amount of insulin the patient that is to be delivered to patient 12 to accommodate the consumption of the meal. Accommodate the consumption of the meal may refer to delivering the amount of insulin that is needed to counteract the increase in glucose level due to consuming the meal. In some examples, the partial therapy dosage may be a preselected therapy dosage, and processing circuitry 32 may be configured to determine the remaining therapy dosage based on one or more of a glucose level measurement or an amount of carbohydrates predicted to consumed by patient 12. For example, the patient behavior pattern may indicate how many carbohydrates patient 12 consumes at different times and/or locations, and processing circuitry 32 may predict an amount of carbohydrates patient 12 is to consume. In some examples, an amount of insulin for the partial therapy dosage is less than an amount of insulin for the remaining therapy dosage.

There may be various ways in which processing circuitry 32 may output instructions to cause the insulin delivery device (e.g., insulin pump 14) to deliver the partial therapy dosage. As one example, processing circuitry 32 may output an instruction to the insulin delivery device to reduce a patient glucose target to cause the insulin delivery device to deliver the partial therapy dosage.

Telemetry circuitry 38 includes any suitable hardware, firmware, software or any combination thereof for communicating with another device, such as cloud 26, insulin pump 16 or injection device 30, as applicable, wearable device 22, and sensor 20. Telemetry circuitry 38 may receive communication with the aid of an antenna, which may be internal and/or external to patient device 24. Telemetry circuitry 38 may be configured to communicate with another computing device via wireless communication techniques, or direct communication through a wired connection. Examples of local wireless communication techniques that may be employed to facilitate communication between patient device 24 and another computing device include RF communication according to IEEE 802.11, Bluetooth, or BLE specification sets, infrared communication, e.g., according to an IrDA standard, or other standard or proprietary telemetry protocols. Telemetry circuitry 38 may also provide connection with carrier network for access to cloud 26. In this manner, other devices may be capable of communicating with patient device 24.

Power source 39 delivers operating power to the components of patient device 24. In some examples, power source 39 may include a battery, such as a rechargeable or non-rechargeable battery. A non-rechargeable battery may be selected to last for several years, while a rechargeable battery may be inductively charged from an external device, e.g., on a daily or weekly basis. Recharging of a rechargeable battery may be accomplished by using an alternating current (AC) outlet or through proximal inductive interaction between an external charger and an inductive charging coil within patient device 24.

Figure 5:
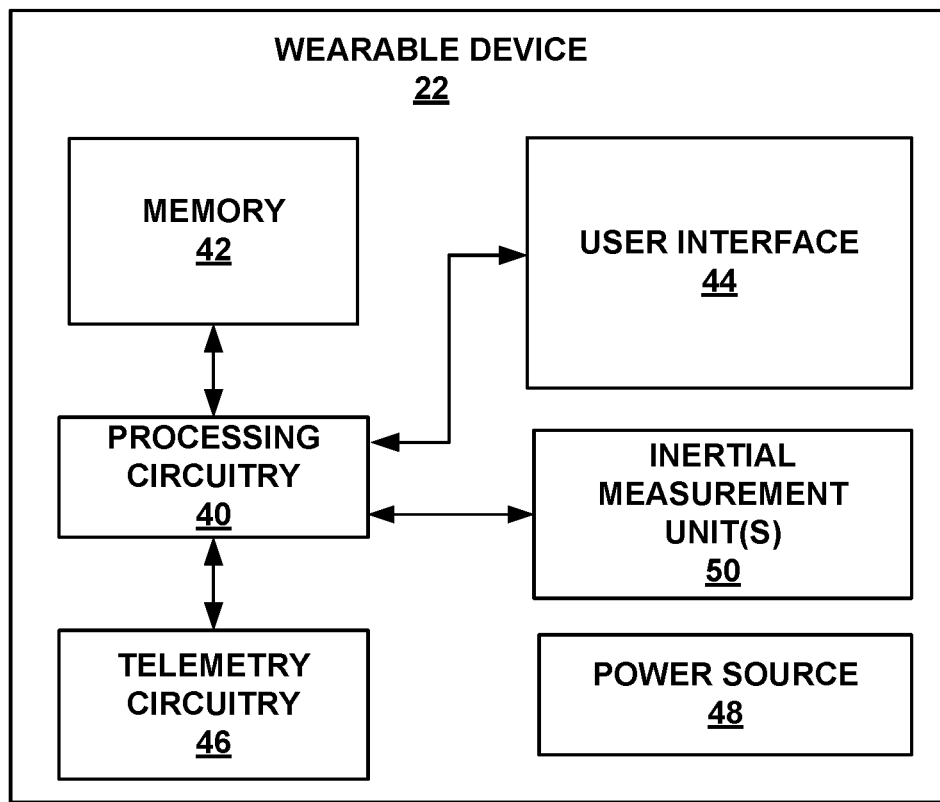
FIG. 5 is a block diagram illustrating an example of a wearable device, in accordance with one or more examples described in this disclosure.

FIG. 5 is a block diagram illustrating an example of a wearable device, in accordance with one or more examples described in this disclosure. As illustrated, wearable device 22 includes processing circuitry 40, memory 42, user interface 44, telemetry circuitry 46, power source 48, and inertial measurement units 50. Processing circuitry 40, memory 42, user interface 44, telemetry circuitry 46, and power source 48 may be similar to processing circuitry 32, memory 34, user interface 36, telemetry circuitry 38, and power source 39 of FIG. 3, respectively.

Inertial measurement units 50 may include accelerometers and gyroscopes and/or various components to determine a pitch-roll-yaw, and x-y-z coordinate of wearable device 22. In some examples, inertial measurement units 50 may be considered as a six-axis inertial measurement unit. For example, inertial measurement units 50 may couple a 3-axis accelerometer with a 3-axis gyroscope. The accelerometer may measure linear acceleration, while the gyroscope may measure rotational motion. Processing circuitry 40 may be configured to determine one or more movement characteristics based on values from inertial measurement units 50. For example, processing circuitry 40 may determine based on values from inertial measurement units 50 if patient 12 is moving his or her arm upwards, downwards, leftwards, rightwards, forwards, backwards, or some combination, including values related to frequency, amplitude, trajectory, position, velocity, acceleration, and/or pattern of movement. Processing circuitry 40 may determine based on values from inertial measurement units 50 orientation of the arm of patient 12, such as whether the back of the hand or the front of the hand is facing patient 12, or if a side of the hand is facing patient 12, such that the thumb is facing patient 12 and the side of the index finger is visible.

As one example, when patient 12 is holding chopsticks to eat, patient 12 may orient his or her wrist in a particular manner, which may be different than if patient 12 is holding a sandwich. The frequency of patient 12 moving his or her arm from a position where he or she is reaching food to a position where he or she is placing food in mouth may be different for different types of food. For example, the frequency and pattern of movement of eating with a fork may be different than eating with a spoon or a knife and fork, which may be different than eating with hands, like a sandwich or pizza. For all of these different food items, there may be a difference in the movement characteristics, and different output values from inertial measurement units 50. However, for all of the movement characteristics, one or more processors (including processing circuitry 40 in some examples) may be configured to determine that patient 12 is eating.

Inertial measurement units 50 may output such information (e.g., pitch-roll-yaw and x-y-z coordinates) of the arm of patient 12 to processing circuitry 40. Telemetry circuitry 46 may then output the information from processing circuitry 40 to patient device 24. Patient device 24 may forward the information to one or more processors 28 that can use the information to determine if patient 12 is eating (e.g., if a meal event is occurring).

Figure 6:
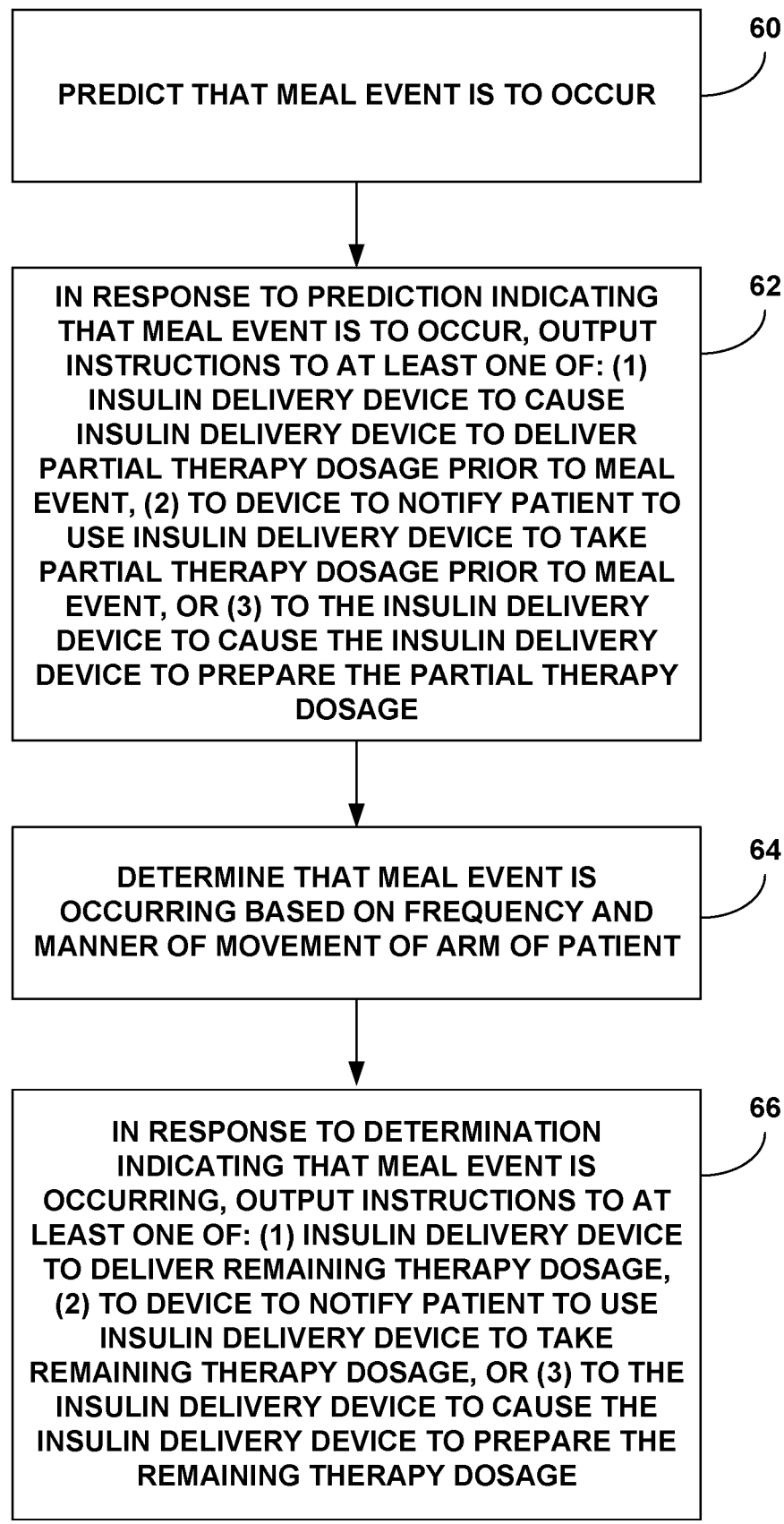
FIG. 6 is a flowchart illustrating an example method of operation, in accordance with one or more examples described in this disclosure.

FIG. 6 is a flowchart illustrating an example method of operation, in accordance with one or more examples described in this disclosure. FIG. 6 is described with respect to one or more processors. The one or more processors may be one or more processors 28, one or more processors of patient device 24 (e.g., processing circuitry 32), one or more processors of wearable device 22 (e.g., processing circuitry 40), one or more processors of insulin pump 14 (if available), or any combination thereof.

One or more processors may predict that a meal event is to occur (60). For example, the one or more processors may be a first set of one or more processors (e.g., one or more processors 28 on one or more servers of cloud 26) that receive information indicative of at least one of time of day or location of patient 12, and that determine (e.g., predict) that the meal event is to occur based on the received information.

In response to the prediction (e.g., determination) indicating that the meal event is to occur, the one or more processors may output instructions to at least one of: (1) the insulin delivery device (e.g., insulin pump 14) to cause the insulin delivery device to deliver a partial therapy dosage prior to the meal event occurring, (2) to a device (e.g., patient device 24 or injection device 30) to notify the patient to use the insulin delivery device to take the partial therapy dosage prior to the meal event occurring, or (3) to the insulin delivery device to cause the insulin delivery device to prepare the partial therapy dosage prior to the meal event occurring (62). In this way, patient 12 may receive a partial amount of insulin to reduce the chances of postprandial increases in glucose level.

One or more processors may determine that the meal event is occurring based on one or more characteristics of movement of an arm of patient 12 (64). The one or more characteristic may correlated with one or more different forms of eating (e.g., the manner and frequency of movement of the arm algins with manner and frequency of movement of arm when patient 12 is eating). For example, a second set of processors (e.g., processing circuitry 40 and inertial measurement units 50) may be configured to determine movement characteristics of patient 12. The first set of processors or the second set of processors may receive the information of one or more movement characteristics, and may determine if the movement characteristics align with movement characteristics for eating. If the movement characteristics align with movement characteristics when patient 12 is eating, the one or more processors (e.g., first set and/or second set of processors) may be determine that the meal event is occurring.

In some examples, the one or more processors may also utilize contextual information to determine that the meal event is occurring, in addition to or instead of, one or more characteristics of movement of an arm of patient 12. For example, the contextual information, such as time of day or location, may provide additional confidence that patient 12 is eating when one or more characteristics of movement of an arm of patient 12 indicate that patient 12 is eating. As an example, if the time is noon and patient 12 is at a restaurant, and the one or more characteristics of movement of an arm of patient 12 indicates that patient 12 is eating, there is more confidence that patient 12 is eating as compared to if only the one or more characteristics of movement of an arm of patient 12 indicates that patient 12 is eating.

In response to the determination indicating that the meal event is occurring, the one or more processors may output instructions to at least one of: (1) the insulin delivery device (e.g., insulin pump 14, injection device 30) to deliver a remaining therapy dosage (with or without further user input at the insulin delivery device), (2) to the device (e.g., patient device 24 and/or injection device 30) to notify patient 12 to use the insulin delivery device to administer the remaining therapy dosage (e.g., via insulin pen or syringe), to the insulin delivery device to cause the insulin delivery device to prepare the partial remaining dosage (66). In some examples, the partial therapy dosage may be a portion of an amount of insulin that is to be delivered to the patient to accommodate the consumption of the meal, and the remaining therapy dosage may be a remaining portion of the amount of insulin the patient that is to be delivered to the patient to accommodate the consumption of the meal. As described above, accommodate the consumption of the meal may refer to delivering the amount of insulin that is needed to counteract the increase in glucose level due to consuming the meal. In some examples, the partial therapy dosage may be a preselected therapy dosage, and the one or more processors may be configured to determine the remaining therapy dosage based on one or more of a glucose level measurement (e.g., from sensor 20) or an amount of carbohydrates predicted to be consumed by patient 12 (e.g., predicted based on behavior patterns). In some examples, an amount of insulin for the partial therapy dosage is less than an amount of insulin for the remaining therapy dosage.

Figure 7A:
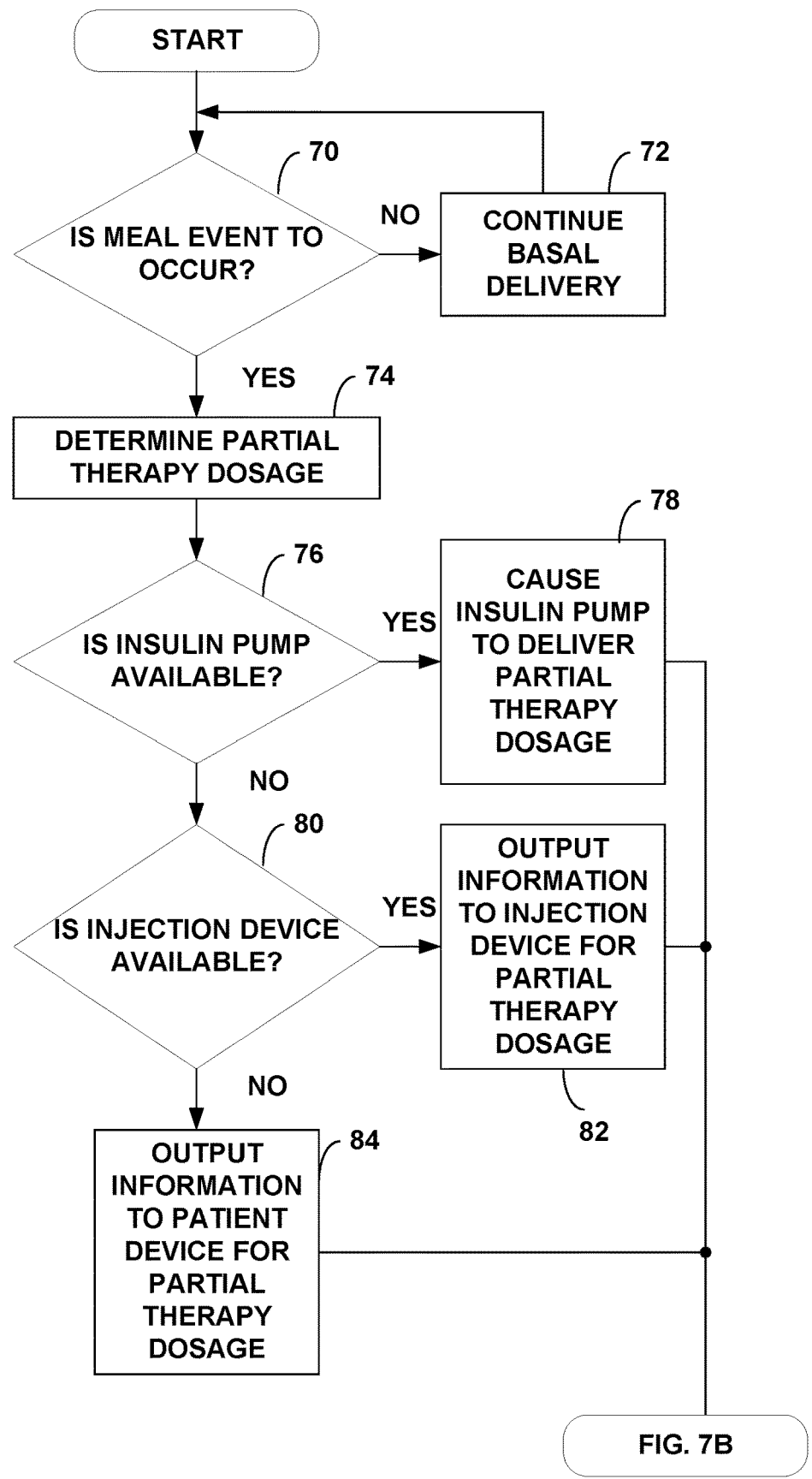
FIGS. 7A and 7B are flowcharts illustrating another example method of operation, in accordance with one or more examples described in this disclosure.
Figure 7B:
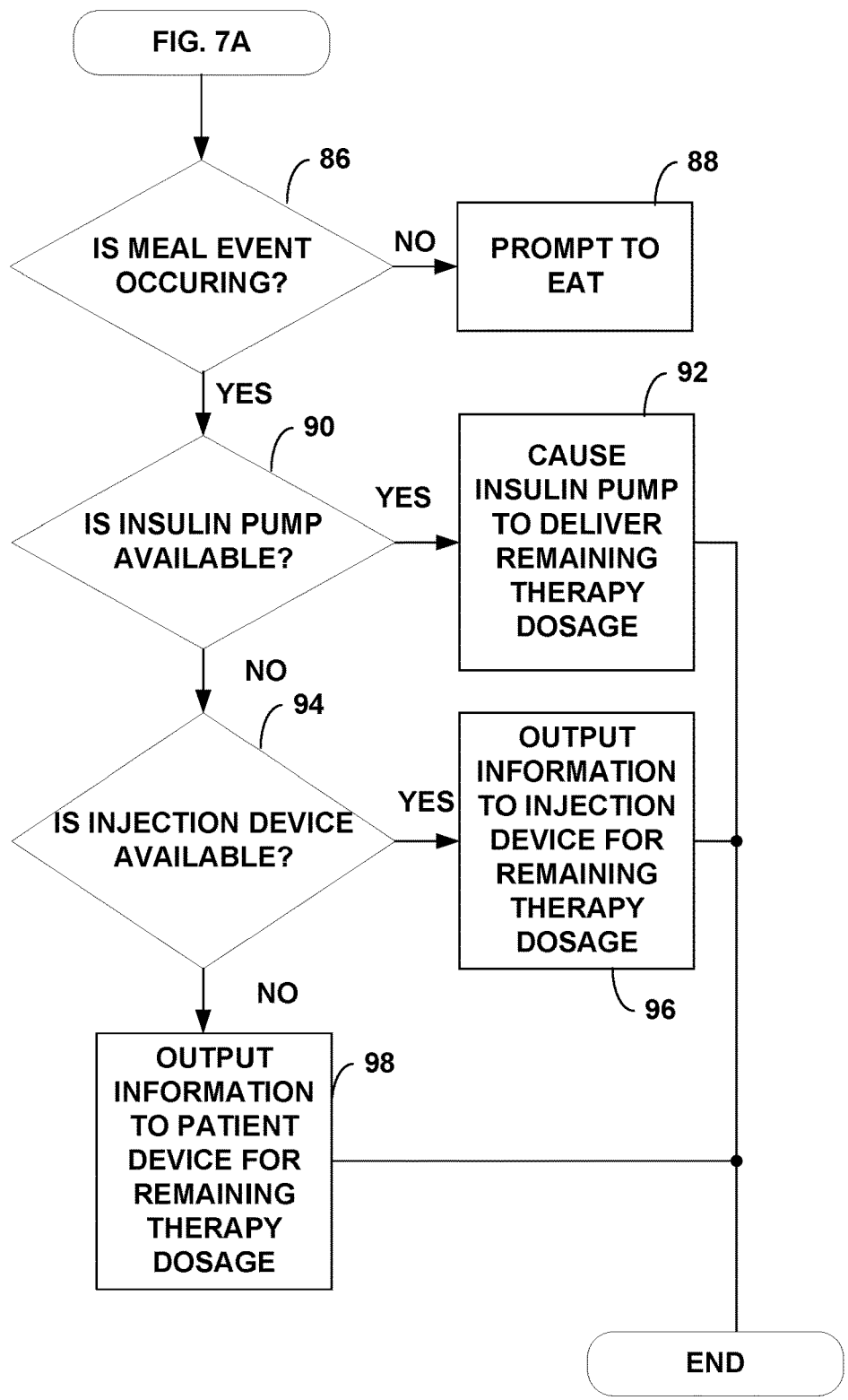

FIGS. 7A and 7B are flowcharts illustrating another example method of operation, in accordance with one or more examples described in this disclosure. Similar to FIG. 6, FIGS. 7A and 7B are described with respect to one or more processors. The one or more processors may be one or more processors 28, one or more processors of patient device 24 (e.g., processing circuitry 32), one or more processors of wearable device 22 (e.g., processing circuitry 40), one or more processors of insulin pump 14 (if available), or any combination thereof.

As illustrated in FIG. 7A, one or more processors may predict (e.g., determine) whether a meal event is to occur (70). For instance, the one or more processors may determine whether the meal event is to occur based on contextual information such as time of day and/or location of a patient 12. If the one or more processors determine that the meal event is not to occur (NO branch of 70), there may be no change in insulin delivery, and patient 12 may continue with delivery of basal insulin (72). As illustrated in FIG. 7A, during the delivery of basal insulin (e.g., baseline therapy), the one or more processors may continuously determine (e.g., predict) whether a meal event is to occur (70).

If the one or more processors predict that a meal event is to occur (YES branch of 70), the one or more processors may determine partial therapy dosage (74). For example, the one or more processors may determine an amount of partial therapy dosage and the time to deliver the partial therapy dosage. In some examples, if only a few (e.g., one or two) items of the contextual information indicated that a meal event is to occur, then the one or more processors may determine a first amount of partial therapy dosage to deliver. However, if more than few of the contextual information indicated that a meal event is to occur, then the one or more processors may determine a second amount of partial therapy dosage to deliver. The second amount of partial therapy dosage may be larger than the first amount of partial therapy dosage. As one example, the second amount of partial therapy dosage may be equal to the first amount of partial therapy dosage plus a preselected additional amount of bolus insulin.

Accordingly, to predict that the meal event is to occur, the one or more processors may receive one or more contextual information of the patient, and determine an amount of partial therapy dosage based on a number of contextual information that is received. In some examples, the one or more processors may determine an amount of partial therapy dosage based on a number and/or quality of contextual information of patient 12. For example, certain types of contextual information may be more predictive of meal events than others. As one example, time of day may be more predictive of meal events than location. In some examples, if the contextual information for patient 12 indicates time of day, then the one or more processors may set a higher dosage amount for the partial dosage than if the context information for patient 12 is only location.

In some examples, the one or more processors may utilize a digital twin of patient 12 to determine the amount of partial therapy dosage and a time to deliver the partial therapy dosage. For instance, the digital twin may have previously determined the therapy dosage based on how many carbohydrates patient 12 consumed, and the one or more processors may predict how many carbohydrates patient 12 is anticipated to consume and when, and based on therapy dosage previously determined by the digital twin, determine the partial therapy dosage and when the partial therapy dosage is to be (or should be) delivered.

If insulin pump 14 is available, such as in FIG. 1, (YES branch of 76), the one or more processors may cause insulin pump 14 (e.g., via patient device 24) to deliver the partial therapy dosage (78). In some examples, the one or more processors may request confirmation or rejection of the partial therapy dosage before insulin pump 14 administers the partial therapy dosage. If insulin pump 14 is not available (NO branch of 76), but injection device 30 is available (YES branch of 80), such as in FIG. 3, the one or more processors may output information to injection device 30 for the partial therapy dosage (82). Injection device 30 may then prepare the injection without additional user input (e.g., automatically load in the correct amount of insulin), and patient 12 may utilize injection device 30 to inject himself or herself. In addition, patient device 24 may also output information of the time when patient 12 is to take the partial therapy dosage and notify patient 12 to take the partial therapy dosage.

If injection device 30 is not available (NO branch of 80), then patient 12 may utilize a syringe or insulin pen to deliver the partial therapy dosage. For example, the one or more processors may output information to patient device 24, wearable device 22, and/or a smart insulin pen cap for the partial therapy dosage, and patient 12 may then use the syringe or insulin pen to deliver the partial therapy dosage based on the information that patient device 24 outputs via user interface 36. In some examples, the output information may include the time when patient 12 is to take the partial therapy dosage.

Turning to FIG. 7B, after patient 12 receives the partial therapy dosage before the meal event, the one or more processors may determine whether the meal event is occurring (86). For instance, the one or more processors may determine whether the meal event is occurring based on one or more movement characteristics detected by wearable device 22. If the meal event is not occurring (NO branch of 86), the one or more processors may output a prompt (e.g., via patient device 24) to instruct patient 12 to eat (88).

However, such prompting may not be necessary because the amount of the partial therapy dosage may not be sufficiently high so as to cause negative impact from low glucose level.

If the meal event is occurring (YES branch of 86) and insulin pump 14 is available (YES branch of 90), then the one or more processors may cause insulin pump 14 to deliver the remaining therapy dosage (92). If insulin pump 14 is not available (NO branch of 90) and injection device 30 is available (YES branch of 94), the one or more processors may output information to injection device 30, wearable device 22, and/or a smart insulin pen cap for the remaining therapy dosage (96), and patient 12 may inject himself or herself with injection device 30. If injection device 30 is not available (NO branch of 94), then the one or more processors may output information to patient device 24 for the remaining therapy dosage (98), and patient 12 may utilize a syringe or insulin pen to inject himself or herself.

The above describes various example techniques. As additional techniques, the type of activity that patient 12 engages in may impact the amount of glucose in the patient's bloodstream. As one example, if patient 12 engages in aerobic exercise, patient 12 tends to use the glucose in his or her bloodstream, and the overall glucose level in the bloodstream may drop. However, if patient 12 engages in anerobic exercise, patient 12 tends to release glucose from muscles into the bloodstream, which can cause the overall glucose level in the bloodstream to increase. Accordingly, if patient 12 is engaging in or will engage in aerobic exercise, the amount of insulin patient 12 is to receive may be reduced or delayed until after exercising. However, if patient 12 is engaging in or will engage in anerobic exercise, the amount of insulin patient 12 is to receive may be increased.

One or more processors 28, but any combination of processors may be utilized, may sense a type of exercise in which patient 12 is engaging or will engage. For example, wearable devices 24 may output information indicating movement characteristics, and one or more processors 28 may determine the type of exercise patient 12 is engaged in based on the information indicating the movement characteristics. As another example, one or more processors 28 may predict, based on patient behavior pattern, whether patient 12 is going to exercise and the type of exercise in which the patient will engage. As another example, one or more processors 28 may determine that patient 12 is engaging exercise based on the heart rate.

In one or more examples, there may be sensors on patient 12 to measure heart rate (e.g., via wearable device 22). One or more processors 28 may determine a high confidence that an exercise event has started (e.g., based on heart rate information or other movement characteristics from wearable device 22). One or more processors 28 may determine if aerobic exercise is under-way or if anerobic exercise is under-way. For aerobic exercise, one or more processors 28 may increase glucose target level, and for anaerobic exercise, one or more processors 28 may decrease glucose target level.

In some examples, one or more processors 28 may determine whether patient 12 has fallen sleep (e.g., based on inertial measurement units in wearable device 22). One or more processors 28 may automatically adjust settings based on patient 12 sleeping. For example, one or more processors 28 may adjust the glucose target level for sleep mode. One or more processors 28 may also reduce the alerts to only ones determined for safety. Although described with one or more processors 28, the example techniques may be performed by any one or combination of one or more processors of the various components described in this disclosure.

As described above, there may be various sensors used to measure different contextual information. The following provides some example ways in which the sensor information may be utilized. For example, based on movement characteristics, one or more processors 28 may determine how much and when to deliver insulin. In some examples, one or more processors 28 may withhold prompts to patient 12, such as low battery, or other types of alerts like if glucose is slightly out of range, based on the sensor data, such as withhold prompts if patient 12 is driving or sleeping. The sensors may indicate changes in temperature, and one or more processors 28 may set the target glucose level based on the temperature. The sensors may indicate with patient 12 is exercising, and one or more processors 28 may set target glucose levels based on if patient 12 is exercising, and if patient 12 is performing aerobic or anerobic exercises.

In some examples, when patient device 24 and/or wearable device 22 output information (e.g., broadcast) to one or more processors 28 may be based on contextual information of patient 12, such as biometrics, location, and time of day. In some examples, patient device 24 and/or wearable device 22 may output information in a way that conserves power (e.g., broadcasting during sleep can be reduced).

There may be other ways in which to utilize information of location of patient 12 to assist with controlling glucose levels. As one example, patient device 24 may, based on the location of patient 12 being that patient 12 is at a grocery store, output information of foods or food companies that provide product that helps treat diabetes.

The following describes various examples that may be utilized together or in combination.

Example 1: A system for therapy delivery includes one or more processors configured to: predict that a meal event is to occur, in response to the prediction indicating that the meal event is to occur, output instructions to at least one of: (1) an insulin delivery device to cause the insulin delivery device to deliver a partial therapy dosage prior to the meal event occurring, (2) to a device to notify the patient to use the insulin delivery device to take the partial therapy dosage prior to the meal event occurring, or (3) to the insulin delivery device to cause the insulin delivery device to prepare the partial therapy dosage prior to the meal event occurring, determine that the meal event is occurring based on one or more movement characteristics of movement of an arm of the patient, and in response to the determination indicating that the meal event is occurring, output instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

Example 2: The system of example 1, wherein the one or more processors comprises a first set of one or more processors on one or more servers and a second set of one or more processors on a wearable device worn by the patient, wherein to predict that a meal event is to occur, the first set of one or more processors is configured to: receive one or more contextual information of the patient, and determine that the meal event is to occur based on the received information, wherein to determine that the meal event is occurring, at least one of the first set of processors or the second set of processors is configured to determine that the meal event is occurring based on the one or more movement characteristics.

Example 3: The system of any of examples 1 and 2, wherein the partial therapy dosage comprises a portion of an amount of insulin that is to be delivered to the patient to accommodate consumption of the meal, and wherein the remaining therapy dosage comprises a remaining portion of the amount of insulin the patient that is to be delivered to the patient to accommodate consumption of the meal.

Example 4: The system of any of examples 1-3, wherein an amount of insulin for the partial therapy dosage is less than an amount of insulin for the remaining therapy dosage.

Example 5: The system of any of examples 1-4, wherein the instruction to the insulin delivery device to cause the insulin delivery device to deliver the partial therapy dosage comprises an instruction to the insulin delivery device to reduce a patient glucose target to cause the insulin delivery device to deliver the partial therapy dosage.

Example 6: The system of any of examples 1-5, wherein the partial therapy dosage comprises a preselected therapy dosage, and wherein the one or more processors are configured to determine the remaining therapy dosage based on one or more of a glucose level measurement or an amount of carbohydrates predicted to be consumed by the patient.

Example 7: The system of any of examples 1-6, further comprising a patient device, wherein at least one of the one or more processors is a processor of the patient device.

Example 8: The system of any of examples 1-7, wherein to predict that the meal event is to occur, the one or more processors are configured to receive one or more contextual information of the patient, wherein the one or more processors are configured to determine an amount of partial therapy dosage based on a number of contextual information that is received.

Example 9: The system of any of examples 1-8, further comprising the insulin delivery device, wherein the insulin delivery device comprises at least one of an insulin pump or an injection device.

Example 10: The system of any of examples 1-9, further comprising: a glucose sensor, wherein the one or more processors are configured to, in response to the determination that the meal event is occurring, instruct the glucose sensor to output a glucose level of the patient at a first rate that is higher than a second rate at which the glucose sensor outputs the glucose level of the patient when the meal event is not occurring.

Example 11: The system of any of examples 1-10, wherein the one or more processors are configured to: determine an amount of carbohydrates the patient is to eat during the meal event and a number of bites the patient will take during the meal event; and based on the determination of the amount of carbohydrates the patient is to eat and the number of bites the patient will take, output instructions to cause the insulin delivery device to deliver a micro-bolus or a series of micro-boluses of insulin therapy during the meal event.

Example 12: The system of example 11, wherein to output the instructions to cause the insulin delivery device to deliver the series of micro-boluses, the one or more processors are configured to output instructions to cause the insulin delivery device to deliver the series of micro-boluses with every detected bite or in regular intervals of time.

Example 13: A method comprising: predicting, with one or more processors, that a meal event is to occur, in response to the prediction indicating that the meal event is to occur, outputting, with the one or more processors, instructions to at least one of: (1) an insulin delivery device to cause the insulin delivery device to deliver a partial therapy dosage prior to the meal event occurring, (2) to a device to notify the patient to use the insulin delivery device to take the partial therapy dosage prior to the meal event occurring, or (3) to the insulin delivery device to cause the insulin delivery device to prepare the partial therapy dosage prior to the meal event occurring, determining, with the one or more processors, that the meal event is occurring based on one or more movement characteristics of movement of an arm of the patient, and in response to the determination indicating that the meal event is occurring, outputting, with the one or more processors, instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

Example 14: The method of example 13, wherein the one or more processors comprises a first set of one or more processors on one or more servers and a second set of one or more processors on a wearable device worn by the patient, wherein predicting that a meal event is to occur comprises: receiving, with the first set of one or more processors, one or more contextual information of the patient; and determining, with the first set of one or more processors, that the meal event is to occur based on the received information, wherein determining that the meal event is occurring comprises determining, with at least one of the first set of one or more processors or the second set of one or more processors, that the meal event is occurring based on the one or more movement characteristics.

Example 15: The method of any of examples 13 and 14, wherein the partial therapy dosage comprises a portion of an amount of insulin that is to be delivered to the patient to accommodate consumption of the meal, and wherein the remaining therapy dosage comprises a remaining portion of the amount of insulin the patient that is to be delivered to the patient to accommodate consumption of the meal.

Example 16: The method of any of examples 13-15, wherein an amount of insulin for the partial therapy dosage is less than an amount of insulin for the remaining therapy dosage.

Example 17: The method of any of examples 13-16, wherein the instruction to the insulin delivery device to cause the insulin delivery device to deliver the partial therapy dosage comprises an instruction to the insulin delivery device to reduce a patient glucose target to cause the insulin delivery device to deliver the partial therapy dosage.

Example 18: The method of any of examples 13-17, wherein the partial therapy dosage comprises a preselected therapy dosage, the method further comprising determining, with the one or more processors, the remaining therapy dosage based on one or more of a glucose level measurement or an amount of carbohydrates predicted to be consumed by the patient.

Example 19: The method of any of examples 13-18, wherein predicting that the meal event is to occur comprises receiving one or more contextual information of the patient, the method further comprising determining an amount of partial therapy dosage based on a number of contextual information that is received.

Example 20: A computer-readable storage medium storing instructions thereon that when executed cause one or more processors to: predict that a meal event is to occur, in response to the prediction indicating that the meal event is to occur, output instructions to at least one of: (1) the insulin delivery device to deliver a partial therapy dosage prior to the meal event occurring, (2) to the device to notify the patient to use the insulin delivery device to take the partial therapy dosage prior to the meal event occurring, or (3) to the insulin delivery device to cause the insulin delivery device to prepare the partial therapy dosage prior to the meal event occurring, determine that the meal event is occurring based on one or more movement characteristics of movement of an arm of the patient, and in response to the determination indicating that the meal event is occurring, output instructions to at least one of: (1) the insulin delivery device to deliver a remaining therapy dosage, (2) to the device to notify the patient to use the insulin delivery device to take the remaining therapy dosage, or (3) to the insulin delivery device to cause the insulin delivery device to prepare the remaining therapy dosage.

Various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, electrical stimulators, or other devices. The term "processor" or "processing circuitry" may generally refer to any of the foregoing logic circuitry, alone or in combination with other logic circuitry, or any other equivalent circuitry.

In one or more examples, the functions described in this disclosure may be implemented in hardware, software, firmware, or any combination thereof. If implemented in software, the functions may be stored on, as one or more instructions or code, a computer-readable medium and executed by a hardware-based processing unit. Computer-readable media may include computer-readable storage media forming a tangible, non-transitory medium. Instructions may be executed by one or more processors, such as one or more DSPs, ASICs, FPGAs, general purpose microprocessors, or other equivalent integrated or discrete logic circuitry. Accordingly, the term "processor," as used herein may refer to one or more of any of the foregoing structure or any other structure suitable for implementation of the techniques described herein.

In addition, in some aspects, the functionality described herein may be provided within dedicated hardware and/or software modules. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components. Also, the techniques could be fully implemented in one or more circuits or logic elements. The techniques of this disclosure may be implemented in a wide variety of devices or apparatuses, including one or more processors 28 of cloud 26, one or more processors of patient device 24, one or more processors of wearable device 22, one or more processors of insulin pump 14, or some combination thereof. The one or more processors may be one or more integrated circuits (ICs), and/or discrete electrical circuitry, residing in various locations in the example systems described in this disclosure.

The one or more processors or processing circuitry utilized for example techniques described in this disclosure may be implemented as fixed-function circuits, programmable circuits, or a combination thereof. Fixed-function circuits refer to circuits that provide particular functionality, and are preset on the operations that can be performed. Programmable circuits refer to circuits that can be programmed to perform various tasks, and provide flexible functionality in the operations that can be performed. For instance, programmable circuits may execute software or firmware that cause the programmable circuits to operate in the manner defined by instructions of the software or firmware. Fixed-function circuits may execute software instructions (e.g., to receive parameters or output parameters), but the types of operations that the fixed-function circuits perform are generally immutable. In some examples, the one or more of the units may be distinct circuit blocks (fixed-function or programmable), and in some examples, the one or more units may be integrated circuits. The processors or processing circuitry may include arithmetic logic units (ALUs), elementary function units (EFUs), digital circuits, analog circuits, and/or programmable cores, formed from programmable circuits. In examples where the operations of the processors or processing circuitry are performed using software executed by the programmable circuits, memory accessible by the processors or processing circuitry may store the object code of the software that the processors or processing circuitry receive and execute.

Various aspects of the disclosure have been described. These and other aspects are within the scope of the following claims.

What is claimed is:

1. A system for therapy delivery, the system comprising:
one or more processors configured to:
predict that a meal event is to occur;
determine an amount of insulin to deliver to a patient to accommodate consumption of a meal;
in response to the prediction indicating that the meal event is to occur, output instructions to at least one of: (1) an insulin delivery device to cause the insulin delivery device to deliver a partial therapy dosage prior to the meal event occurring, (2) a device to notify the patient to use the insulin delivery device to take the partial therapy dosage prior to the meal event occurring, or (3) the insulin delivery device to cause the insulin delivery device to prepare the partial therapy dosage prior to the meal event occurring, wherein the partial therapy dosage comprises a portion of the determined amount of insulin that is to be delivered to the patient to accommodate consumption of the meal;
determine that the meal event is occurring based on one or more movement characteristics of movement of an arm of the patient; and
in response to the determination indicating that the meal event is occurring, output instructions to at least one of: (1) the insulin delivery device to deliver a remaining therapy dosage, (2) the device to notify the patient to use the insulin delivery device to take the remaining therapy dosage, or (3) the insulin delivery device to cause the insulin delivery device to prepare the remaining therapy dosage, wherein the remaining therapy dosage comprises a remaining portion of the determined amount of insulin that is to be delivered to the patient to accommodate consumption of the meal.

2. The system of claim 1,
wherein the one or more processors comprises a first set of one or more processors on one or more servers and a second set of one or more processors on a wearable device worn by the patient,
wherein to predict that a meal event is to occur, the first set of one or more processors is configured to:
receive one or more contextual information of the patient; and determine that the meal event is to occur based on the received contextual information,
wherein to determine that the meal event is occurring, at least one of the first set of processors or the second set of processors is configured to determine that the meal event is occurring based on the one or more movement characteristics.

3. The system of claim 1, wherein the partial therapy dosage is less than the remaining therapy dosage.

4. The system of claim 1, wherein the instruction to the insulin delivery device to cause the insulin delivery device to deliver the partial therapy dosage comprises an instruction to the insulin delivery device to reduce a patient glucose target to cause the insulin delivery device to deliver the partial therapy dosage.

5. The system of claim 1, wherein the partial therapy dosage comprises a preselected therapy dosage, and wherein the one or more processors are configured to determine the remaining therapy dosage based on one or more of a glucose level measurement or an amount of carbohydrates predicted to be consumed by the patient.

6. The system of claim 1, further comprising a patient device, wherein at least one of the one or more processors is a processor of the patient device.

7. The system of claim 1, wherein to predict that the meal event is to occur, the one or more processors are configured to receive one or more contextual information of the patient, wherein the one or more processors are configured to determine an amount of partial therapy dosage based on a number of contextual information that is received.

8. The system of claim 1, further comprising the insulin delivery device, wherein the insulin delivery device comprises at least one of an insulin pump or an injection device.

9. The system of claim 1, further comprising:
a glucose sensor,
wherein the one or more processors are configured to, in response to the determination that the meal event is occurring, instruct the glucose sensor to output a glucose level of the patient at a first rate that is higher than a second rate at which the glucose sensor outputs the glucose level of the patient when the meal event is not occurring.

10. The system of claim 1, wherein the one or more processors are configured to:
determine an amount of carbohydrates the patient is to eat during the meal event and a number of bites the patient will take during the meal event; and
based on the determination of the amount of carbohydrates the patient is to eat and the number of bites the patient will take, output instructions to cause the insulin delivery device to deliver a micro-bolus or a series of micro-boluses of insulin therapy during the meal event.

11. The system of claim 10, wherein to output the instructions to cause the insulin delivery device to deliver the series of micro-boluses, the one or more processors are configured to output instructions to cause the insulin delivery device to deliver the series of micro-boluses with every detected bite or in regular intervals of time.

12. A method comprising:
predicting, with one or more processors, that a meal event is to occur;
determining, with the one or more processors, an amount of insulin to deliver to a patient to accommodate consumption of a meal;
in response to the prediction indicating that the meal event is to occur, outputting, with the one or more processors, instructions to at least one of: (1) an insulin delivery device to cause the insulin delivery device to deliver a partial therapy dosage prior to the meal event occurring, (2) a device to notify the patient to use the insulin delivery device to take the partial therapy dosage prior to the meal event occurring, or (3) the insulin delivery device to cause the insulin delivery device to prepare the partial therapy dosage prior to the meal event occurring, wherein the partial therapy dosage comprises a portion of the determined amount of insulin that is to be delivered to the patient to accommodate consumption of the meal;
determining, with the one or more processors, that the meal event is occurring based on one or more movement characteristics of movement of an arm of the patient; and
in response to the determination indicating that the meal event is occurring, outputting, with the one or more processors, instructions to at least one of: (1) the insulin delivery device to deliver a remaining therapy dosage, (2) the device to notify the patient to use the insulin delivery device to take the remaining therapy dosage, or (3) the insulin delivery device to cause the insulin delivery device to prepare the remaining therapy dosage, wherein the remaining therapy dosage comprises a remaining portion of the determined amount of insulin that is to be delivered to the patient to accommodate consumption of the meal.

13. The method of claim 12,
wherein the one or more processors comprises a first set of one or more processors on one or more servers and a second set of one or more processors on a wearable device worn by the patient,
wherein predicting that a meal event is to occur comprises:
receiving, with the first set of one or more processors, one or more contextual information of the patient; and
determining, with the first set of one or more processors, that the meal event is to occur based on the received contextual information,
wherein determining that the meal event is occurring comprises determining, with at least one of the first set of one or more processors or the second set of one or more processors, that the meal event is occurring based on the one or more movement characteristics.

14. The method of claim 12, wherein the partial therapy dosage is less than the remaining therapy dosage.

15. The method of claim 12, wherein the instruction to the insulin delivery device to cause the insulin delivery device to deliver the partial therapy dosage comprises an instruction to the insulin delivery device to reduce a patient glucose target to cause the insulin delivery device to deliver the partial therapy dosage.

16. The method of claim 12, wherein the partial therapy dosage comprises a preselected therapy dosage, the method further comprising determining, with the one or more processors, the remaining therapy dosage based on one or more of a glucose level measurement or an amount of carbohydrates predicted to be consumed by the patient.

17. The method of claim 12, wherein predicting that the meal event is to occur comprises receiving one or more contextual information of the patient, the method further comprising determining an amount of partial therapy dosage based on a number of contextual information that is received.

18. The method of claim 12, further comprising:
  determining an amount of carbohydrates the patient is to eat during the meal event and a number of bites the patient will take during the meal event; and
  based on the determination of the amount of carbohydrates the patient is to eat and the number of bites the patient will take, outputting instructions to cause the insulin delivery device to deliver a micro-bolus or a series of micro-boluses of insulin therapy during the meal event.

19. The method of claim 18, wherein outputting the instructions to cause the insulin delivery device to deliver the series of micro-boluses comprises outputting instructions to cause the insulin delivery device to deliver the series of micro-boluses with every detected bite or in regular intervals of time.

20. A computer-readable storage medium storing instructions thereon that when executed cause one or more processors to:
  predict that a meal event is to occur;
  determine an amount of insulin to deliver to a patient to accommodate consumption of a meal;
  in response to the prediction indicating that the meal event is to occur, output instructions to at least one of: (1) an insulin delivery device to cause the insulin delivery device to deliver a partial therapy dosage prior to the meal event occurring, (2) a device to notify the patient to use the insulin delivery device to take the partial therapy dosage prior to the meal event occurring, or (3) the insulin delivery device to cause the insulin delivery device to prepare the partial therapy dosage prior to the meal event occurring, wherein the partial therapy dosage comprises a portion of the determined amount of insulin that is to be delivered to the patient to accommodate consumption of the meal;
  determine that the meal event is occurring based on one or more movement characteristics of movement of an arm of the patient; and
  in response to the determination indicating that the meal event is occurring, output instructions to at least one of: (1) the insulin delivery device to deliver a remaining therapy dosage, (2) the device to notify the patient to use the insulin delivery device to take the remaining therapy dosage, or (3) the insulin delivery device to cause the insulin delivery device to prepare the remaining therapy dosage, wherein the remaining therapy dosage comprises a remaining portion of the determined amount of insulin that is to be delivered to the patient to accommodate consumption of the meal.

* * * * *